United States Patent
Mansouri et al.

(10) Patent No.: US 7,455,760 B2
(45) Date of Patent: Nov. 25, 2008

(54) ANALYTICAL INSTRUMENTS, BIOSENSORS AND METHODS THEREOF

(75) Inventors: Sohrab Mansouri, Sudbury, MA (US); Vasile Cosofret, Acton, MA (US); Clarke Xu, Maynard, MA (US)

(73) Assignee: Instrumentation Laboratory Company, Lexington, MA (US)

( * ) Notice: Subject to any disclaimer, the term of this patent is extended or adjusted under 35 U.S.C. 154(b) by 467 days.

(21) Appl. No.: 11/049,251

(22) Filed: Feb. 2, 2005

(65) Prior Publication Data

US 2005/0126929 A1    Jun. 16, 2005

Related U.S. Application Data

(63) Continuation of application No. 09/871,885, filed on May 31, 2001, now Pat. No. 6,872,297.

(51) Int. Cl.
  *G01N 27/38* (2006.01)
  *G01N 27/327* (2006.01)
(52) U.S. Cl. .................. 205/778; 205/775; 204/402
(58) Field of Classification Search ..............
        204/403.01–403.05, 402; 205/775, 777.5,
                                     205/778, 792
  See application file for complete search history.

(56) References Cited

U.S. PATENT DOCUMENTS

| | | | |
|---|---|---|---|
| 4,109,505 A * | 8/1978 | Clark et al. ............... 73/1.02 |
| 4,214,968 A | 7/1980 | Battaglia et al. ............ 204/418 |
| 4,355,105 A | 10/1982 | Lantero, Jr. ................. 435/94 |
| 4,390,627 A | 6/1983 | Lantero, Jr. ................. 435/180 |
| 4,431,507 A | 2/1984 | Nankai et al. ............... 204/403 |
| 4,551,482 A | 11/1985 | Tschang et al. .............. 521/53 |
| 4,713,165 A | 12/1987 | Conover et al. ............. 204/403 |
| 4,734,184 A | 3/1988 | Burleigh et al. ............. 204/409 |
| 4,760,024 A | 7/1988 | Lantero, Jr. ................. 435/178 |
| 4,810,351 A | 3/1989 | Chapoteau et al. .......... 204/418 |
| 4,950,378 A | 8/1990 | Nagata ....................... 204/402 |
| 5,132,345 A | 7/1992 | Harris et al. ................. 524/108 |
| 5,162,077 A | 11/1992 | Bryan et al. ................. 204/402 |
| 5,212,050 A | 5/1993 | Mier et al. .................. 430/320 |
| 5,262,305 A | 11/1993 | Heller et al. ............. 205/780.5 |
| 5,286,364 A | 2/1994 | Yacynych et al. ........... 204/418 |
| 5,326,449 A | 7/1994 | Cunningham ............... 204/403 |
| 5,352,349 A | 10/1994 | Inamoto et al. ......... 204/153.12 |
| 5,403,451 A | 4/1995 | Riviello et al. ........... 205/777.5 |

(Continued)

FOREIGN PATENT DOCUMENTS

DE        195 00 354 C1        10/1995

(Continued)

OTHER PUBLICATIONS

Borsook et al., "Oxidation-Reduction Potential of Ascorbic acid (Vitamin C)", Proc. Natl. Acad. Sci. U.S.A. 19(9) 875-878.*

(Continued)

*Primary Examiner*—Alex Noguerola
(74) *Attorney, Agent, or Firm*—K & L Gates LLP

(57) ABSTRACT

An electrochemical sensor system and membrane and method thereof for increased accuracy and effective life of electrochemical and enzyme sensors.

14 Claims, 9 Drawing Sheets

U.S. PATENT DOCUMENTS

| | | | | |
|---|---|---|---|---|
| 5,411,647 | A | 5/1995 | Johnson et al. | 205/777.5 |
| 5,498,323 | A | 3/1996 | Lewenstam et al. | 205/780.5 |
| 5,540,828 | A | 7/1996 | Yacynych | 204/418 |
| 5,541,097 | A | 7/1996 | Lantero et al. | 435/188 |
| 5,653,862 | A | 8/1997 | Parris | 205/777.5 |
| 5,766,934 | A | 6/1998 | Guiseppi-Elie | 435/287.9 |
| 5,798,030 | A | 8/1998 | Raguse et al. | 204/403 |
| 6,030,827 | A | 2/2000 | Davis et al. | 435/287.1 |
| 6,051,389 | A | 4/2000 | Ahl et al. | 435/10 |
| 6,133,229 | A | 10/2000 | Gibson et al. | 514/2 |
| 6,214,185 | B1 | 4/2001 | Offenbacher et al. | 204/403 |
| 6,275,717 | B1 * | 8/2001 | Gross et al. | 600/345 |
| 6,413,396 | B1 | 7/2002 | Yang et al. | 204/403.4 |
| 6,478,950 | B1 | 11/2002 | Peat et al. | 205/775 |
| 6,652,720 | B1 | 11/2003 | Mansouri et al. | 204/403.11 |
| 6,872,297 | B2 | 3/2005 | Mansouri et al. | 205/775 |

FOREIGN PATENT DOCUMENTS

| | | |
|---|---|---|
| EP | 0 125 136 A2 | 11/1984 |
| EP | 0133531 A1 | 2/1985 |
| EP | 0133531 B1 | 2/1985 |
| EP | 0396788 A1 * | 11/1990 |
| EP | 0 771 867 A2 | 5/1997 |
| EP | 0 909 952 A2 | 4/1999 |
| FR | 2792726 | 10/2000 |
| GB | 2 194 843 A | 3/1988 |
| JP | 60-155959 | 8/1985 |
| JP | 60155959 | 8/1985 |
| JP | 01028555 | 1/1989 |
| JP | 3-85435 | 4/1991 |
| JP | 3-156358 | 7/1991 |
| JP | 2001-025717 | 1/2001 |
| WO | 93/06237 | 4/1993 |
| WO | 94/20841 | 9/1994 |
| WO | 97/15827 | 5/1997 |
| WO | WO 01/65248 A2 | 9/2001 |

OTHER PUBLICATIONS

Borsook et al., "Oxidation-Reduction Potential of Ascorbic acid (Vitamin C)", Proc. Natl. Acad. Sci. U.S.A. 19(9) 875-878, 1933.*

Andersson et al., (1999) "Protein Stabilising Effect of Polyethyleneimine" *Journal of Biotechnology*, vol. 72, pp. 21-31.

Cao et al., (1996) "Enhancing Enzymatic Properties by the Information Method" *Applied Biochemistry and Biotechnology*, vol. 59, No. 1.

Chen et al., (1998) "Stability of Oxidases Immobilized in Silica Gels" *J. Am. Chem. Soc.*, vol. 120, pp. 4582-4585.

Emneus et al., (1993) "Comparison Between Different Inorganic Supports for the Immobilization of Amyloglucosidase and a-amylase to Be Used in Enzyme Reactors in Flo-Injections Systems" *Analytica Chimica Acta*, vol. 276, pp. 303-318.

European Examination Report for European Patent Application No. 02747870.0, issued Sep. 29, 2004.

Garcia et al., (1990) "An Immobilization Technique Yielding High Enzymatic Load on Nylon Nets", *Biotechnology Techniques*, vol. 4, No. 6, pp. 425-428.

Geise et al., (1991) "Electropolymerized Films to Prevent Interferences and Electrode Fouling in Biosensors" *Biosensors & Bioelectronics*, vol. 6, pp. 151-160.

Ghindilis et al., (1994) "Glucose Potentiometric Electrodes Based on Mediatorless Bioelectrocatalysis. A New Approach", *Biosensors & Bioelectronics*, vol. 9, pp. 353-357.

Hart et al., (1999) "Estimation of Lactate in Meat Extracts by Screen-Printed Sensors," *Analytica Chimica Acta*, vol. 386, pp. 7-12.

Heller et al., (1998) "Loss of Activity or Gain in Stability of Oxidases Upon Their Immobilization in Hydrated Silica: Significant of the Electrostatic Interaction of Surface Arginine Residues at the Entrances of the Reaction Channels" *J. Am. Chem. Soc.* 1998, vol. 120, pp. 4586-4590.

Ikariyama et al., "Polypyrrole Electrode as a Detector for Electroinactive Anions by Flow Injection Analysis," *Anal. Chem.*, vol. 58 (1986) pp. 1803-1806.

International Search Report for International Application No. PCT/US02/16818, issued Jun. 12, 2003.

Lim et al., "Gas Permeable Membranes Composed of Carboxylated Poly(vivyl chloride) and Polyurethane." *Bull. Korean Chem. Soc.*, 20, 672-76 (1999).

Mádáras et al., "Miniaturized Biosensors Employing Electropolymerized Permselective Films and Their Use for Creatinine Assays in Human Serum," *Anal. Chem.*, vol. 68 (1996) pp. 3832-3839.

Mansouri et al., (1998) "Development of a Glucose Sensor and Its Inclusion in the GEM Blood Analyzer" *International Federation of Clinical Chemistry and Laboratory Medicine* OmniPress.

Minagawa et al., (1998) "Development of Long Life Lactate Sensor Using Thermostable Mutant Lactate Oxidase" *Biosensors and Bioelectronics*, vol. 13, No. 3-4, pp. 313-318.

Moody et al., "PVC Matrix Membrane Ion-Selective Electrodes." *J. Chem Educ.*, 51, 541-44 (1974).

Oh et al., "Potassium-Selective PVC Membrane Electrodes Based on Newly Synthesized cis- and trans- Bis(crown ether)s" *Anal. Sci.*, 14, 1009-12 (Oct. 1998).

Partel et al., (2000) "Fabrication and Characterization of Disposable Type Lactate Oxidase Sensors for Dairy Products and Clinical Analysis," *Sensors and Actuators*, vol. B 67, pp. 134-141.

Sasso et al., (1990) "Electropolymerized 1, 2-Diaminobenzene as a Means to Prevent Interferences and Fouling and To Stabilize Immobilized Enzyme in Electrochemical Biosensors" *Analytical Chemistry*, vol. 62, No. 11.

Umezawa et al., "Potentiometric Selectivity Coefficients of Ion-Selective Electrodes: Part 1. Inorganic Cations." *Pure Appl. Chem.*, 72, 1851-56 (2000).

Yang et al., (1999) "Needle-type Lactate Biosensor" *Biosensors and Bioelectronics*, vol. 14, pp. 203-210.

Bott, Adrian W. (1998) "Electrochemical Methods for the Determination of Glucose", *Current Separations*, vol. 17, No. 1, pp. 25-31.

European Examination Report for European Patent Application No. 02747870.0, issued Feb. 2, 2005.

* cited by examiner

ANALYTICAL INSTRUMENTS, BIOSENSORS AND METHODS THEREOF

This application is a continuation of application Ser. No. 09/871,885, filed on May 31, 2001, now U.S. Pat. No. 6,872,297, the entire disclosure of which is incorporated by reference herein.

FIELD OF THE INVENTION

The present invention is related to the field of electrochemical sensors, particularly enzyme-electrode sensors, and to the regeneration or maintenance of the functional properties of the membranes of such sensors.

BACKGROUND OF THE INVENTION

In a variety of clinical situations it is important to measure certain chemical characteristics of the patient's blood such as pH, hematocrit, the ion concentration of calcium, potassium, chloride, sodium, glucose, lactate, creatinine, creatine, urea, the partial pressure of $O_2$, and $CO_2$, and the like. These situations range from a routine visit of a patient in a physician's office to monitoring of a patient during open-heart surgery. The required speed, accuracy, and other performance characteristics vary with each situation.

Typically, electrochemical sensor systems which provide blood chemistry analysis are stand-alone machines or are adapted to be connected to an extracorporeal shunt or an ex vivo blood source such as a heart/lung machine used to sustain a patient during surgery. Thus, for example, small test samples of ex vivo blood can be diverted off-line from either the venous or arterial flow lines of a heart/lung machine directly to a chamber exposed to a bank of micro-electrodes which generate electrical signals proportional to chemical characteristics of the real time flowing blood sample.

Electrochemical sensor systems are analytical tools combining a chemical or biochemical recognition component (e.g., an enzyme) with a physical transducer such as a platinum electrode. The chemical or biochemical recognition component is capable of selectively interacting with an analyte of interest and of generating, directly or indirectly, an electrical signal through the transducer. Electrochemical sensor systems play an increasing role in solving analytical and clinical problems, and find applications in the field of medical diagnostics.

The selectivity of certain biochemical recognition components makes it possible to develop electrochemical sensors which can accurately detect certain biological analytes even in a complex analyte mixture such as whole blood. Despite the high degree of selectivity of certain biochemical recognition components, the selectivity of such sensors as a whole may nonetheless be compromised by the presence of certain biological interferents (e.g. ascorbic acid, uric acid, acetaminophen, cysteine, etc.) which can directly interact with the physical transducer if they are not prevented from doing so. Accuracy and precision of electrochemical sensor systems with biochemical recognition compounds is also compromised by residual levels of analyte remaining in the sensor from a prior sample affecting the analysis of the following sample.

SUMMARY OF THE INVENTION

One objective of the present invention is to provide a system and method for increasing the accuracy and effective lifetime of an electrochemical sensor. Polymerization of electropolymerizable monomers into an inner polymeric membrane on the electrochemical sensor forms an interference rejection membrane. This inner polymeric membrane functions to protect the electrochemical sensor from the fouling or interference by compounds in the sample and thus increase the accuracy that is lost by the fouling degradation of the membrane or by interference by analyte compounds from the sample.

In one aspect of the present invention, an electrochemical sensor includes at least one electrode, and a composite membrane. The composite membrane includes an outer layer, an enzyme layer, and a restorable inner layer. The inner layer is in contact with at least one electrode and includes a polymerizable membrane.

The outer layer of the composite membrane may include a compound selected from the group consisting of polyurethane-based compounds, polyvinyl-based compounds, silicone elastomer-based compounds, and polycarbonate-based compounds. In one embodiment, the enzyme layer of the electrochemical sensor includes a $H_2O_2$ generating enzyme, such as glucose oxidase or lactate oxidase, for example. In another embodiment, the enzyme layer includes one or a combination of several enzymes, such as a mixture of glucose oxidase, lactate oxidase, creatininase, creatinase, and sarcosine oxidase. In one embodiment, the electrochemical sensor further includes a restored surface on the inner layer wherein the surface is restored by polymerized monomer. The inner layer of the electrochemical sensor may include a compound selected from the group consisting of benzothiophene, phenylenediamines, and dihydroxybenzenes.

In one aspect of the present invention, an electrochemical sensor cartridge, includes an electrochemical sensor card, at least one electrochemical sensor, and a reservoir containing an electropolymerizable monomer solution in fluid communication with the electrochemical sensor card.

In an embodiment of the present invention, the electrochemical sensor cartridge may include an electrochemical sensor card that includes at least one composite membrane. In another embodiment, the electrochemical sensor cartridge may include a composite membrane with a restorable inner layer.

In an embodiment of the present invention, the electrochemical sensor cartridge includes at least one calibration solution reservoir in fluid communication with the electrochemical sensor card. In another embodiment the electropolymerizable monomer solution may be combined with the calibration solution in a single reservoir. In another embodiment of the present invention, the electrochemical sensor cartridge includes electropolymerizable monomer solution in the calibration solution wherein the concentration of the monomer is in the range of about 1-100 mM.

In another embodiment, at least one of the electrochemical sensors of the electrochemical sensor cartridge comprises an enzyme electrode sensor. In another embodiment the electrochemical sensor of the electrochemical sensor cartridge is formed on an electrode composed from a material selected from a group consisting of platinum, gold, carbon or one of their modified structure. In another embodiment the electrochemical sensor includes an electropolymerizable monomer selected from a group consisting of benzothiophene, phenylenediamines, and dihydroxybenzenes. In another embodiment the electrochemical sensor is selective for a hydrogen ion, carbon dioxide, oxygen, sodium ion, potassium ion, ionized calcium, chloride, hematocrit, glucose, lactate, creatine, creatinine or urea. In yet another embodiment, the electrochemical sensor includes a electropolymerizable monomer that is a derivative of phenylenediamine.

In another aspect of the present invention, an electrochemical sensor system includes an electrochemical sensor card including at least one electrochemical sensor, wherein the electrochemical sensor includes at least one polymeric membrane. The electrochemical sensor system also includes an electrochemical sensor apparatus that is in electrical contact with the electrochemical sensor card. The electrochemical sensor apparatus is configured to measure electrical signals from the electrochemical sensor card and is capable of providing an electrical potential to the electrochemical sensor for the polymerization of the electropolymerizable monomer solution to the polymeric membrane. The electrochemical sensor system also includes a reservoir containing an electropolymerizable monomer solution in fluid communication with the electrochemical sensor card. The electropolymerizable monomer solution is polymerized to the polymeric membrane by the electrical potential provided by the electrochemical sensor apparatus.

In an embodiment of the present invention, the electrochemical sensor cartridge may include an electrochemical sensor card that includes at least one composite membrane. In another embodiment, the electrochemical sensor cartridge may include a composite membrane with a restorable inner layer.

In an embodiment, the electrochemical sensor system further includes a calibration solution in a reservoir in combination with an electropolymerizable monomer solution. The concentration of the electropolymerizable monomer solution is in the range of about 1-100 mM. In another embodiment, the electrochemical sensor system includes at least one enzyme electrode sensor. In yet another embodiment, the electrochemical sensor system includes an electrochemical sensor that is selective for a compound selected from a group consisting of hydrogen ion, carbon dioxide, oxygen, sodium ion, potassium ion, ionized calcium, chloride, hematocrit, glucose, lactate, creatine, creatinine or urea.

In yet another embodiment, the electrochemical sensor system includes an electropolymerizable monomer that is selected from a group consisting of benzothiophene, phenylenediamines, and dihydroxybenzenes, of which the concentration of the electropolymerizable monomer solution in the calibration solution is 1-100 mM. In another embodiment, electrochemical sensor system includes an electrochemical sensor apparatus capable of providing an electrical potential for at least the partial removal of interfering agents in the polymeric membrane. In another embodiment, electrochemical sensor system further includes an outer membrane and an enzyme layer, in which the enzyme layer is in contact with the outer membrane and the polymeric membrane.

In another aspect, the invention relates to accelerating the recovery of the electrochemical sensor during the rinse process following exposure to a sample so that the recovery time of the electrochemical sensor system in a shorter time period. The reduction in recovery time is accomplished by removing interfering agents from the polymeric membrane layer. Residual concentration of substrates for the enzymatic reaction and the products of the enzymatic reaction after exposure of the electrochemical sensor to a sample, are examples of interfering agents. Another example of interfering agents is the residual concentration of the electropolymerizable monomer in the polymeric membrane after exposure of the electrochemical sensor to the electropolymerizable monomer solution.

The removal of interfering agents from a polymeric membrane is accomplished by providing an electrochemical sensor including an electrode and a composite membrane, the composite membrane including at least one polymeric membrane, an electrical source in electrical contact with said electrode, and by applying an electrical potential to the electrode sufficient to cause at least a portion of the interfering agents in the polymeric membrane in contact with the electrode to be removed. In one embodiment, the electrical potential is in a range of about 0.1 to 0.8 V versus the on-board reference electrode and is applied for a range of time from about 10 to 200 seconds. In another embodiment, the electrical potential is about 0.4 V versus the on-board reference electrode and is applied for about 50 seconds.

In another aspect, the invention relates to the method of restoring the functional properties of an electrochemical sensor. The method includes providing an electrochemical system, which includes an electrochemical sensor card including at least one electrochemical sensor. The electrochemical sensor includes an electrode and a composite membrane, the composite membrane including at least one polymeric membrane. The electrochemical sensor system also includes an electrochemical sensor apparatus in electrical contact with the electrochemical sensor card. The electrochemical sensor apparatus is configured to measure electrical signals from the electrochemical sensor card and to provide an electrical potential to the electrochemical sensor. The electrochemical sensor system also includes a reservoir containing an electropolymerizable monomer in a solution in fluid communication with the electrochemical sensor card. The electropolymerizable monomer solution is polymerized to the polymeric membrane by the electrical potential provided by the electrochemical sensor apparatus. The method of restoring the functional properties of an electrochemical sensor also includes contacting the electrochemical sensor with the solution and applying an electrical potential of sufficient strength and sufficient duration to cause at least a portion of the electropolymerizable monomer in the solution to polymerize onto the polymeric membrane.

In an embodiment, the method of restoring the functional properties of an electrochemical sensor includes adding the electropolymerizable monomer to a calibrating solution to form the electropolymerizable monomer solution. In one embodiment, the electrical potential comprises a range of about 0.1 to 0.8 V versus the on-board reference electrode and is applied for a range of time from about 30 seconds to 1 hour. In another embodiment, the electrical potential comprises about 0.5 V versus an on-board reference electrode and is applied for about 3 minutes.

In an embodiment, the method of restoring the functional properties of an electrochemical sensor further includes the step of applying an additional electrical potential of sufficient strength and sufficient duration to the electrode to cause removal of at least a portion of interfering agents in the polymeric membrane. In one embodiment, the electrical potential is in a range of about 0.1 to 0.8 V versus the on-board reference electrode and is applied for a range of time from about 10 to 200 seconds.

In another aspect, the invention relates to the method for restoring the functional properties of an electrochemical sensor cartridge. The method includes the steps of connecting an electrochemical sensor cartridge that includes an electrochemical sensor to an electrochemical sensor apparatus. The electrochemical sensor includes an electrode and a composite membrane, which includes at least one polymeric membrane. The method further includes contacting the electrochemical sensor with electropolymerizable monomer solution from the cartridge, and applying an electrical potential of sufficient strength and sufficient duration to cause at least a portion of the electropolymerizable monomer solution to polymerize onto a polymeric membrane. In one embodiment, the method further includes adding an electropolymerizable monomer to a calibrating solution to form the electropolymerizable monomer solution. In a particular embodiment, an electrical potential is applied at a range of about 0.1 to 0.8 V versus the on-board reference electrode. The electrical potential may be applied for a range of time from about 30 seconds to 1 hour. In one embodiment, the method also includes applying an additional electrical potential of sufficient strength and sufficient duration to the electrode to cause removal of at least a portion of interfering agents in the polymeric membrane. In one embodiment, the electrical potential is in a range of about 0.1 to 0.8 V versus the on-board reference electrode and is applied for a range of time from about 10 to 200 seconds.

In another aspect, the invention relates to a composite membrane for a biosensor. The biosensor includes an inner membrane layer, an outer membrane layer, and an enzyme layer. The enzyme layer includes a matrix that includes at least one enzyme, a cross-linking agent, and an enzyme stabilizer. In one embodiment of the present invention, the composite membrane includes one or more of the enzymes lactate oxidase, creatinase, sarcosine oxidase, and creatininase.

In another aspect, the invention relates to a matrix for an enzyme sensor. The matrix includes lactate oxidase, a cross-linking agent, and a enzyme stabilizer. In one embodiment, the matrix forms a cross-linked matrix of proteins having enzymatic activity. The matrix may form an electrochemical electrode. The matrix may also include bovine serum albumin. Other inert proteins similar to bovine serum albumin may also be included. In another embodiment, one or more of the cross-linking agent present in the matrix may include a dialdehyde, glutaraldehyde, for example, a diisocyanato, 1,4-diisocyanatobutane, for example, and a diepoxide, 1,2,7,8-diepoxyoctane and 1,2,9,10-diepoxydecane, as examples. In another embodiment, the cross-linking agent present in the matrix is 1-10% glutaraldehyde by weight. In yet another embodiment, the cross-linking agent present in the matrix is 5% glutaraldehyde by weight. In another embodiment, the enzyme stabilizer present in the matrix may include one or more of the compounds, polyethyleneimine, polypropyleneimine, poly(N-vinylimidazole), polyallylamine, polyvinylpiridine, polyvinylpyrollidone, polylysine, protamine and their derivatives. In another embodiment, the enzyme stabilizer present in the matrix is 1-20% polyethyleneimine by weight. In another embodiment, the enzyme stabilizer present in the matrix is 5% polyethyleneimine by weight.

In yet another aspect, the invention relates to a matrix for an enzyme sensor that includes creatinase, sarcosine oxidase, a cross-linking agent and, an enzyme stabilizer. In one embodiment, the matrix also includes creatininase. In one embodiment, the matrix forms a cross-linked matrix of proteins having enzymatic activity. The enzyme sensor may form an electrochemical sensor. In another embodiment, one or more of the cross-linking agent present in the matrix may include a dialdehyde, glutaraldehyde, for example, a diisocyanato, 1,4-diisocyanatobutane, for example, and a diepoxide, 1,2,7,8-diepoxyoctane and 1,2,9,10-diepoxydecane, as examples. In another embodiment, the cross-linking agent present in the matrix is 1-10% glutaraldehyde by weight. In yet another embodiment, the cross-linking agent present in the matrix is 5% glutaraldehyde by weight. In another embodiment the enzyme stabilizer present in the matrix may include one or more of the compounds, polyethyleneimine, polypropyleneimine, poly(N-vinylimidazole), polyallylamine, polyvinylpiridine, polyvinylpyrollidone, polylysine, protamine and their derivatives. In another embodiment, the enzyme stabilizer present in the matrix is 1-20% polyethyleneimine by weight. In another embodiment, the enzyme stabilizer present in the matrix is 5% polyethyleneimine by weight.

In yet another aspect, the invention relates to a matrix for an enzyme sensor including one or more of the enzymes, lactate oxidase, creatinase, sarcosine oxidase and creatininase, a cross-linking agent, and an enzyme stabilizer.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWING

The foregoing and other objects, features and advantages of the present invention disclosed herein, as well as the invention itself, will be more fully understood from the following description of preferred embodiments and claims, when read together with the accompanying drawings. The drawings are not necessarily to scale, emphasis instead generally being placed upon illustrating the principles of the invention.

DETAILED DESCRIPTION OF THE INVENTION

Figure 1:
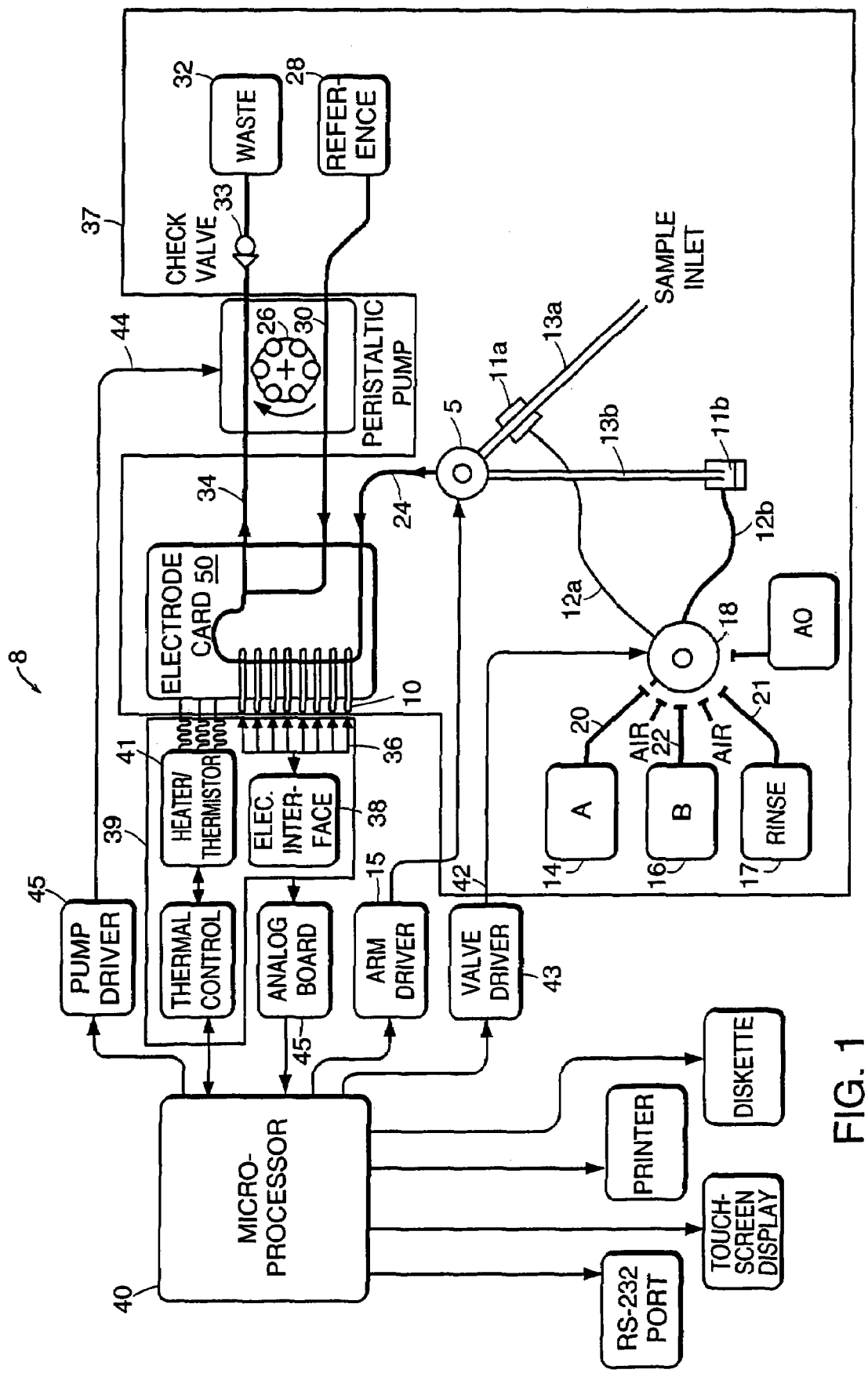
FIG. 1 is a schematic diagram of the components of an electrochemical sensor apparatus including a sensor cartridge with a bank of sensors and a thermal block for accelerated hydration and calibration of the sensors.

The present invention provides electrodes and electrochemical sensor systems for measuring characteristics of aqueous samples including, but not limited to, blood, serum or other body fluids. Specifically, the invention is directed to such sensors in which the electrodes include an interference rejection membrane, which is the inner polymeric membrane of the composite membrane and is renewable in situ. The electrochemical sensor systems according to the invention have increased accuracy and precision and increased effective life spans. In preferred embodiments of the invention, the sensor system is adapted to measure the concentration or activity of blood gases (e.g., oxygen and carbon dioxide) ions (e.g., sodium, chloride, potassium and calcium), glucose, lactate, creatine, creatinine, blood pH and hematocrit.

Definitions

In order to more clearly and concisely point out and describe the subject matter which applicant regards as the invention, the following definitions are provided for certain terms used in the following description and claims.

As used herein, the term "electrode" refers to a component of an electrochemical device which makes the interface between the external electrical conductor and the internal ionic medium. The internal ionic medium, typically, is an aqueous solution with dissolved salts. The medium may also comprise proteins in a stabilizing matrix.

Electrodes are of three types, working or indicator electrodes, reference electrodes, and counter electrodes. A working or indicator electrode measures a specific chemical species, such as an ion. When electrical potentials are measured by a working electrode, the method is termed potentiometry. All ion-selective electrodes operate by potentiometry. When current is measured by a working electrode, the method is termed amperometry. Oxygen measurement is carried out by amperometry. Working electrodes may also function by including an enzyme as part of an enzyme layer that is part of a composite layer that is in close contact with the electrode. The enzyme, which is specific to a particular analyte, produces hydrogen peroxide, a by-product of the catalytic reaction of the enzyme on the analyte. Hydrogen peroxide is detected by the electrode and converted to an electrical signal. A reference electrode serves as an electrical reference point in an electrochemical device against which electrical potentials are measured and controlled. In one embodiment, silver-silver nitrate forms the reference electrodes. Other types of reference electrodes are mercury-mercurous chloride-potassium chloride or silver-silver chloride-potassium chloride. A counter electrode acts as a sink for the current path.

As used herein, the term "sensor" is a device that responds to variations in the concentration of a given chemical species, such as glucose or lactate, in a sample, such as a body fluid sample. An electrochemical sensor is a sensor that operates based on an electrochemical principle and requires at least two electrodes. For ion-selective measurements, the two electrodes include an ion-selective electrode and a reference electrode. Amperometric enzyme electrodes additionally require a third electrode, a counter electrode. Moreover, enzyme sensors based on two electrodes, a working and reference electrode, are also common.

As used herein, the term "ion selective electrode" generally refers to a silver wire coated with silver chloride in contact with a buffer solution containing a chloride concentration (the inner solution). The buffer solution is covered with a polymeric ion-selective membrane that is in contact with the test solution. The ion selective membrane typically consists of a high molecular weight PVC, a plasticizer, an ionophore specific to a particular ion, and a borate salt. The surface of the polymeric membrane is in contact with the test sample on one side and the inner buffer solution on the other side of the membrane.

As used herein, the term "dry electrochemical sensor" refers to the ion selective electrode, described above, and a reference electrode, described above. In the "dry chemical" embodiment, the ion-selective electrodes have the same configuration as described above, however, the inner solution containing chloride, is dried, i.e., dehydrated leaving a layer of dry salt. In order to function as an electrochemical sensor, the dried salt must be solubilized in water to obtain a buffer solution.

As used herein, the term "enzyme electrode" generally refers to a composite membrane deposited on a metal electrode, comprising platinum for example. The composite membrane is at least three distinct layers including an outer polymeric membrane on the side of the composite membrane in contact with the sample that forms a protective layer, a middle enzyme layer that is located between the outer and inner layers, and an inner polymeric membrane closest to the metal electrode that forms the inner interference rejection membrane. The outer polymeric membrane, which is comprised of one or more polymeric compounds, generally functions to protect and maintain the structure of the middle enzyme layer and to control the diffusion of the analyte into the middle enzyme layer. The middle or enzyme layer comprises at least one protein species with enzymatic activity. The enzymatic activity may also be provided by compounds which include DNA, RNA, and carbohydrate, for example. The enzyme is stabilized in a matrix conducive to the activity of the enzyme. The inner or interference rejection membrane is a polymeric membrane that functions to insulate the wire electrode from compounds in the sample that interfere with the functioning and accuracy of the electrode.

As used herein, the term "hydration" refers to the process of solubilizing the salts of a sensor's inner salt layer by the passage of water through the ion-selective outer polymeric membrane bounding one side of the inner salt layer, into the inner salt layer to form a solution. Hydration normally can be achieved by mere contact of the outside of the polymeric membrane and inner salt solution with an aqueous salt solution for a required duration.

As used herein, "thermal cycling" is the process by which the temperature of an electrochemical sensor, soaked in an aqueous salt solution, is raised to a specified elevated temperature for a specified length of time, and then lowered.

As used herein, the term "calibration" refers to the process by which the response characteristics of a sensor to a specific analyte are determined quantitatively. To calibrate a sensor, the sensor is exposed to at least two reagent samples, each reagent sample having a different, known concentration of an analyte. The responses, i.e., signals, measured by the sensor, relative to the concentrations of the analyte in the two different reagent samples, serve as reference points for measurements of the analyte in samples having unknown concentrations of the analyte.

Referring to FIG. 1, the electrochemical sensor system 8 employs a sensor assembly, generally indicated at 10, incorporating a plurality of electrodes adapted to make electrical measurements on a sample, such as a blood sample, introduced to the sensor assembly 10. Blood samples to be analyzed by the system are introduced through a sample inlet 13a. Blood samples are obtained by, for example, phlebotomy or are derived on a periodic basis from an extracorporeal blood flow circuit connected to a patient during, for example, open heart surgery. Blood samples may be introduced into the sample inlet 13a through other automatic means, or manually, as by syringe. The blood samples may be introduced as discrete samples.

The electrochemical system 8 including a number of essential components as heretofore described in a preferred embodiment of the present invention is contained in a disposable cartridge 37. A cartridge of a similar type is set forth in detail in U.S. Pat. No. 4,734,184, the entirety of the specification incorporated by reference herein. In one embodiment of the invention, the electrochemical sensor system 8 incorporates in the cartridge 37 at least two prepackaged containers 14, and 16, each containing a calibrating aqueous solution having known values of the parameters to be measured by the system. For purposes of reference, the solution contained within the prepackaged container 14 will be termed Calibrating Solution A, the solution contained within the prepackaged container 16 will be termed Calibrating Solution B. In another embodiment of the invention, the electrochemical system 8, illustrated in FIG. 1, includes a third prepackaged container 23 containing Calibrating Solution AO. Each of the prepackaged containers 14, 16 and 23 contain a sufficient quantity of its calibrating solution to allow the system to be calibrated a substantial number of times before the prepackaged container becomes empty. When one or more of the containers 14, 16 and 23 containing the calibrating solutions are empty, the cartridge containing prepackaged containers 14, 16 and 23 must be replaced.

In a particular embodiment of the invention, the Calibrating Solution AO contains electropolymerizable monomer. Electropolymerizable monomer such as m-phenylenediamine may be included in the calibrating solutions at a concentration in a range of about 1 to 100 mM, preferably about 15 mM. In another embodiment of the invention, a solution of electropolymerizable monomers is contained in a prepackaged container (not shown) separate from the prepackaged containers 14 and 16 for the calibrated solutions at a concentration in a range of about 1 to 100 mM, preferably about 15 mM.

Referring to FIG. 1, in one embodiment the prepackaged container 14 is connected to the input of a multi-position valve 18 through a flow line 20, and the prepackaged container 16 is connected to a second input of the multi-position valve 18 through a flow line 22. In yet another embodiment, the container 23 is connected to a third input of the multi-position valve 18 through a flow line 25. Another container 17 contains a rinse solution and is connected to the input of the multi-position valve 18 through a flow line 21. In yet another embodiment, the rinse bag 17 is eliminated and one of the calibration solutions A or B is used as a rinse solution, as well. The output line 12 is the output of the multi-position valve 18 and is connected to the sample input line 13 through a stylus 11. Depending upon the position of the valve 18, the input lines 20, 21, 22, 25 or air is open to the valve 18. Similarly, when the stylus is in a normal position (position 11b) of the sample input line 13b, line 12b is open to the sample input line 13b and allows passage of the calibrating, or rinse solution, or air through the sample input line 13b to the sensor assembly 10 through line 24, facilitated by the operation of a peristaltic pump schematically illustrated at 26. However, in a sample accepting mode (13a), line 12 is separated from the sample input line (position 12a) and the sample is introduced directly to the sensor assembly 10 through line 24, facilitated by the operation of the peristaltic pump 26.

The cartridge 37 also includes a container 28, for a reference solution. The container 28 is connected to the sensor assembly by a flow line 30. The system further includes a container 32 for waste, which receives the blood samples, the calibrating solutions and the reference solution after they have passed through the sensor assembly 10, via a flexible conduit 34 that has input from the sensor assembly 10.

Both the waste flow conduit 34 and the reference solution flow line 30 consist of or include sections of flexible walled tubing that pass through the peristaltic pump 26. The pump 26 compresses and strokes the flexible sections of the flow lines 30 and 34 to induce a pressured flow of reference solution from the container 28 to the electrode assembly 10 and to create a negative pressure on the waste products in flow line 34 so as to draw fluids, including the fluids with the polymerizable monomers, in the flow line 24 through passages in the electrode assembly 10 past the membranes of the sensors. This arrangement, as opposed to the alternative of inducing positive pressure on the blood and calibrating solutions to force them through the electrode assembly 10, avoids the imposition of unnecessary and possibly traumatic mechanical forces on the blood sample and minimizes possibilities of leaks in the electrode assembly 10.

Cartridge 37 also contains a sensor card 50 which provides a low volume, gas tight chamber in which the sample, such as a blood sample, calibration solution, or monomer-containing solution, is presented to one or more electrochemical sensors, i.e., the pH, $pCO_2$, $pO_2$, $Na^+$, $Ca^{++}$, glucose, lactate, creatine, creatinine and hematocrit sensors, together with the reference electrode collectively indicated as sensors 10, are integral parts of the chamber. Chemically sensitive, hydrophobic membranes typically formed from polymers, such as polyvinyl chloride, specific ionophores, and a suitable plasticizer, are permanently bonded to the chamber body. These chemically sensitive, hydrophobic membranes, described below in detail, are the interface between the sample or calibrating solutions and the buffer solution in contact with the inner (silver/silver chloride) electrode.

In one embodiment of the invention, referring still to FIG. 1, included in the cartridge 37, are three solutions that allow for calibrations at high and low concentrations for all parameters except hematocrit, which calibrates at one level. In one embodiment, the cartridge 37 also includes the rotor-for-sample inlet arm 5, the pump tubing 24, 30 and 34, the sampling stylus 11, a waste bag 32, the reference solution container 28, the rinse solution container 17, calibration solution containers 14, 16 and 23, the check valve 33, and tubes 12, 20, 21, 22 and 25. Blood samples that have been analyzed are prevented from flowing back into the sensor card 50 from the waste container 32 due to the presence of a one-way check 33 valve in the waste line 34. After use in the system 8, the cartridge 37 is intended to be discarded and replaced by another cartridge.

Referring to FIG. 1, sensors are available as a bank of electrodes 10 fabricated in a plastic card 50 and housed in the disposable cartridge 37 that interfaces with a thermal block assembly 39 of a suitably adapted blood chemistry analysis machine. The thermal block assembly 39 houses the heating/cooling devices such as a resistive element or a Peltier-effect device, a thermistor 41 to monitor and control the temperature, the electrical interface 38 between the sensors in the plastic card 50 and the microprocessor 40 through the analog board 45. The analog board 45 houses analog-to-digital and digital-to-analog converters. The signal from the electrode interface 38 passes through the analog-to-digital converter, converted into digital form for the processor 40 to store and display. Conversely, the digital signals from the processor 40, for example, the polarization voltage for oxygen sensor, go through the digital-to-analog converter, converted into an analog form and fed to the sensors for control, through the electrode interface 38.

The electrochemical sensor system 8 is formed upon insertion of the cartridge 37 into the electrochemical sensor apparatus. Upon insertion, the sensor card 10 fits into the heater block assembly 39, described in detail below, and the heating/cooling assembly regulated by the microprocessor 40 cycles the temperature of the sensor card 50 and the solution in contact with the sensors inside the sensor card 50 through a specific temperature for a specified duration. The heater block assembly 39 is capable of rapid heating and cooling by, for example, a thermoelectric device applying, for example, the Peltier-effect, monitored by a thermistor 41, all controlled by the microprocessor 40. The sensors connect to the electrode interface 38 which select one of the plurality of electrical signals generated by the sensors and passes the electrical signal to the microprocessor 40 in the machine through an analog-to-digital converter into the analog board 45 where it is converted from analog to digital form, suitable for storage and display. Referring to FIG. 1, the electrode assembly 10 has a number of edge connectors 36 in a bank which allow it to be plugged into a female matching connector 38 so that the electrodes formed on the assembly 10 may be connected to microprocessor 40 through the analog board 45. The microprocessor 40 is connected to the multiport valve 18 via a valve driver 43 by a line 42 and to the motor of the peristaltic pump 26 via a pump driver 45 by a line 44. The microprocessor 40 controls the position of the sample arm 5 through arm driver 15, and the position of the valve 18 and the energization of the pump 26 to cause sequences of blood samples and calibrating solutions to be passed through the electrode assembly 10. When the calibrating solutions from, for example, containers 14, 16 and 23 are pumped into the electrode assembly 10, the electrodes forming part of the assembly make measurements of the parameters of the sample and the microprocessor 40 stores these electrical values. Based upon measurements made during the passage of the calibration solutions through the electrode assembly 10, and the known values of the measured parameters contained within the calibrating solution from containers 14, 16, and 23, the microprocessor 40 effectively creates a calibration curve for each of the measured parameters so that when a blood sample is passed through the electrode assembly 10 the measurements made by the electrodes can be used to derive accurate measurements of the parameters of interest. These parameters are stored and displayed by the microprocessor 40. The microprocessor 40 is suitably programmed to perform measurement, calculation, storage, and control functions such as differences in electrical potential across one or more electrodes.

Calibrating Solutions

In one embodiment of the invention a composition of calibrating solution A used for second point calibration, prepared at 37° C. and at atmospheric pressure tonometered with 9% $CO_2$ 14% $O_2$ and 77% Helium gas, is as follows: pH 6.9 organic buffer; $pCO_2$=63 mmHg; $pO_2$=100 mmHg; $Na^+$=100 mmol/L; $K^+$=7 mmol/L; $Ca^{++}$=2.5 mmol/L; glucose=150 mg/dL; lactate=4 mmol/L; creatine=0.5 mmol/L; creatinine=0.5 mmol/L; surfactant and inert preservative.

In another embodiment of the invention a composition of calibration solution B used for one-point calibration and rinse, prepared at 37° C. and at 700 mmHg absolute pressure tonometered with 27% $O_2$, 5% $CO_2$, and 68% Helium gas, is as follows: pH 7.40 organic buffer; $pCO_2$=34 mmHg; $pO_2$=180 mmHg; $Na^+$=140 mmol/L; $K^+$=3.5 mmol/L; $Ca^{++}$=1.0 mmol/L; surfactant and inert preservative.

In yet another embodiment of the invention a preferred composition of calibration solution AO for low level oxygen calibration and in situ regeneration of the inner polymeric membrane for the enzyme sensors contains aqueous solution of $Na^+$, $K^+$, $Ca^{++}$ salt; 15 mmol/L of m-phenylenediamine, 20 mmol/L of sulfite, surfactant and inert preservative; organic buffer, $pCO_2$. The reference solution contains $AgNO_3$=1 mmol/L; $KNO_3$=1 mol/L; surfactant.

The compositions of the A and B calibrating solutions are chosen so that for each of the characteristics measured by the system a pair of values are obtained that are spaced over the range of permissible values that are measured by the system, providing a balanced 2-point calibration for the instrument. The AO calibrating solution is chosen for low level oxygen calibration and regeneration of the inner polymeric membrane in the glucose, creatine, creatinine and lactate sensors.

The A and B calibration compositions are prepared by premixing all of the constituents in a certain order starting with the buffer and ending with the sodium bicarbonate salt, then tonometering the solution with oxygen and $CO_2$ mixed with helium to produce the desired level of $pCO_2$ and $pO_2$. The AO calibration solution is prepared with a slight difference in procedure. The salts with the exception of sodium sulfite, m-phenylenediamine and sodium bicarbonate are added to water and the solution is tonometered with helium to bring the $pO_2$ to less that 30 mmHg. Then, the remaining salts are added to the solution and the final mixture is tonometered with mixture of $pCO_2$ and helium to produce the desired $pCO_2$ level.

At least one electropolymerizable monomer is added to at least one of the calibrating solutions, solution AO in container 23 for example. The absence of dissolved oxygen in the AO solution, due to presence of sulfite ion, allows for a longer shelf life of electropolymerizable monomer in the AO solution because dissolved oxygen will oxidize the electropolymerizable monomer and thus render the monomer incapable of polymerizing. The electropolymerizable monomers m-phenylenediamine for example, may be included in a calibrating solution at a concentration in a range between about 1 to 100 mM, preferably 15 mM. The electropolymerizable monomer may be included in the cartridge 37 in a separate reservoir.

The temperature and pressure at which the calibrating solutions are prepared and their method of packaging must be such as to preclude the possibility of dissolved gases going out of solution in the container, which would affect the concentration of gases in the calibrating solutions, and to minimize the tendency for gases to permeate through even the most impermeable materials practically obtainable. The calibration solutions are packaged with the solutions completely filling the containers, so that there is no head space, by evacuating the containers prior to filling in a manner which will be subsequently described.

By filling the calibration solution into the evacuated flexible wall container 14, 16, 23 at elevated temperatures and subatmospheric pressure, the solution will not have any tendency at a lower use temperature to outgas and thus produce gas bubbles in the container. Were outgassing to occur, the concentrations of the gases in the solution would be affected, creating an inaccuracy in the calibration of the instruments. Similarly, the calibration solutions must not be packaged at too low a pressure i.e., not below about 625 mm of mercury, because the absorptive capacity of the solution for gases conceivably increases as the packaging pressure decreases and below that pressure value the absorptive capacity of the solution may be sufficiently high that it will tend to draw gases in through the slight inherent permeability of even the most gas impervious flexible packaging material, over long periods of time. Accordingly, a packaging pressure in the range of 625-700 mm of mercury is preferred.

In one embodiment, a calibrating solution prepared at a temperature in excess of its intended use temperature so that at the lower temperature there is less tendency for outgassing of the dissolved gases. This cooperates with the reduced pressure packaging to minimize the possibility of outgassing.

Calibration Solution A, B and AO are prepared at a temperature above its intended use temperature at a controlled pressure close to atmospheric pressure. Through use of elevated temperature (e.g., 37° C.) the solution may be prepared at about atmospheric pressure without any possibility of subsequent microbubbles within the container or gas transfer through the container when packaged in a zero head space flexible gas impervious container.

The envelopes which form the calibration solution prepackaged containers 14, 16, 23 are formed, for example, of rectangular sheets, heatsealed at the edges and heatsealed at one corner to an inlet stem of the valve 18 which is used for filling purposes. In the preferred embodiment illustrated, the prepackaged containers 14, 16, and 23 and the prepackaged container lines 20, 22, and 25 are formed in a unitary cluster with the valve 18 so that gas phase dead space in the lines 20, 22, 25 is thereby avoided. In a preferred procedure for purging and filling the envelope bags, the envelope is first evacuated and then filled with the prepared solution. The bag is then shaken while the excess solution continually flows out of the bag. This process removes any residual gas bubbles from the bag. The solution is then sealed in the container.

The calibration solutions in the prepackaged containers 14, 16, and 23 have excellent stability and a long shelf life. When at use temperature and atmospheric pressure there is no possibility of any outgassing from the liquid to form gas bubbles within the prepackaged containers 14, 16, and 23.

Reference Solution

The reference solution disposed in prepackaged container 28 is employed in the electrode assembly 10 as a supply source to a reference electrode to provide a liquid junction and thereby isolate the reference electrode from the varying electrochemical potential of the calibrating solution or the blood in a manner which will be subsequently described. In a preferred embodiment, the solution is 1 mol/L potassium nitrate and 1 mmol/L silver nitrate solution. The solution also contains a surfactant such as Brij 35. The solution is packaged in a sealed flexible container with no head space.

Electrode Assembly

Referring to FIG. 1, during operation of the pump 26, the electrode assembly 10 receives a constant pulsating flow of the reference solution via line 30 and sequential, intermittent pulsating flows of either the blood sample or one of the calibrating solutions via line 24. The assembly also provides a corresponding output of its waste products to a waste collection bag 32 via line 34.

Figure 2:
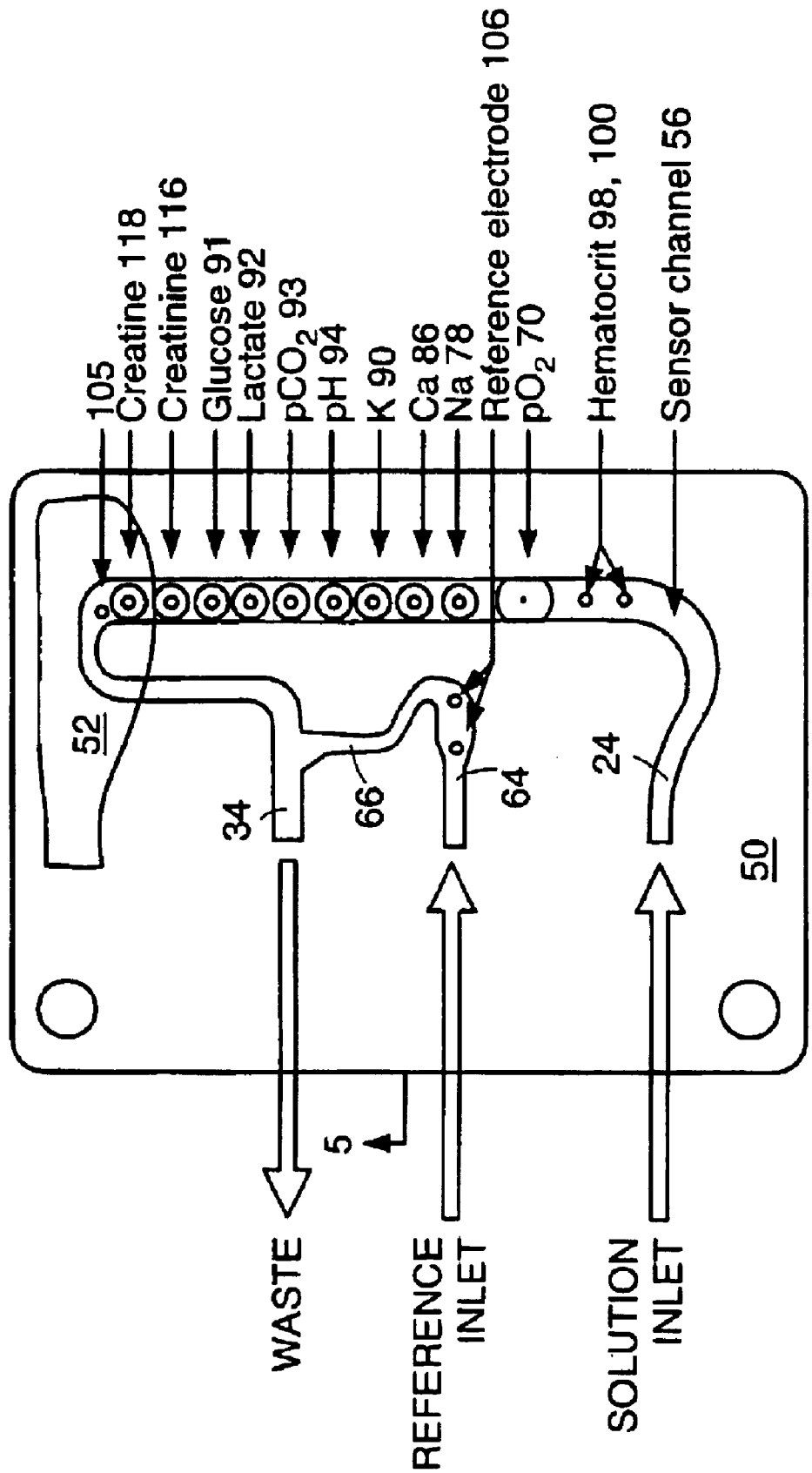
FIG. 2 illustrates a reverse frontal view of the sensor card, partly fragmentary, of a cartridge embodiment of the invention.

Referring to FIG. 2, by way of example, the electrode assembly 10 in a preferred embodiment consists of a structurally rigid rectangular card 50 of polyvinylchloride having a rectangular aluminum (or other suitable material) cover plate 52 adhered to one of its surfaces. Cover plate 52 closes off the flow channels 56 formed in one surface of the card 50 and also acts as a heat transfer medium for hydrating the sensors by thermal cycling, described below, and to maintain the fluids flowing through the electrode assembly 10, and the electrodes themselves, at a constant temperature during calibration and during measurement of relevant parameters in a patient sample. This may be achieved by measuring the temperature of the plate 52 and employing a suitable heating or cooling element e.g., a Peltier-effect device and thermistor 41 to maintain the temperature of the plate 52 at a desired temperature.

Referring to FIG. 2, a reference solution is introduced to a well 64, formed in the surface of the substrate 50 in the same manner as the other flow channels 56 and similarly covered by the metal plate 52. The reference solution flow line 30 passes through an inclined hole in the well 64. The well 64 is connected to the output section 34 of the flow channel 56 through a very thin capillary section 66 formed in the surface of the plastic substrate 50 in the same manner as the main flow channels 56. The capillary channel 66 is substantially shallower and narrower than the main flow channel 56; its cross section is approximately 0.5 sq. mm. Reference fluid pumped into the well 64 by the pump 26, via a line 30 (see also FIG. 1), fills the well, and is forced through the capillary section 66 where it joins the output stream of fluid passing through the main flow channel section 56 and then flows with it to the waste bag 32. The combined influence of its higher density described above and the capillarity of the flow channel 66 serves to minimize any possibility of calibrating solution or blood passing downward through the channel 66 to the well 64 and upsetting the electrochemical measurements.

As a blood sample or calibration solution quantity introduced into the flow channel 24 passes through the flow channel 56 to the output section 34, it passes over a number of electrodes as illustrated in FIG. 2.

Referring to FIGS. 1 and 2, the heat plate 52 abuts and forms one wall of the sample channel 56. The heat plate 52 is in contact with the Peltier-effect device of the thermal block assembly 39 described below. The thermal block assembly 39 is capable of changing and controlling the temperature of the heat plate 52 between 15° C. and 75° C. The temperature change and control is monitored by a thermistor 41 and regulated by the microprocessor 40. An internal digital clock of the microprocessor 40 controls time and can switch on and switch off the thermal block assembly 39 according to a preset program. Thus, microprocessor 40 controls the thermal block assembly 39, regulating the temperature setting and the duration of each set temperature of the heat plate 52.

The Electrodes

The order of assembly of the electrodes given below is only by way of example and is not intended to be limited to the order provided.

The Hematocrit Electrode Pair

Figure 5:
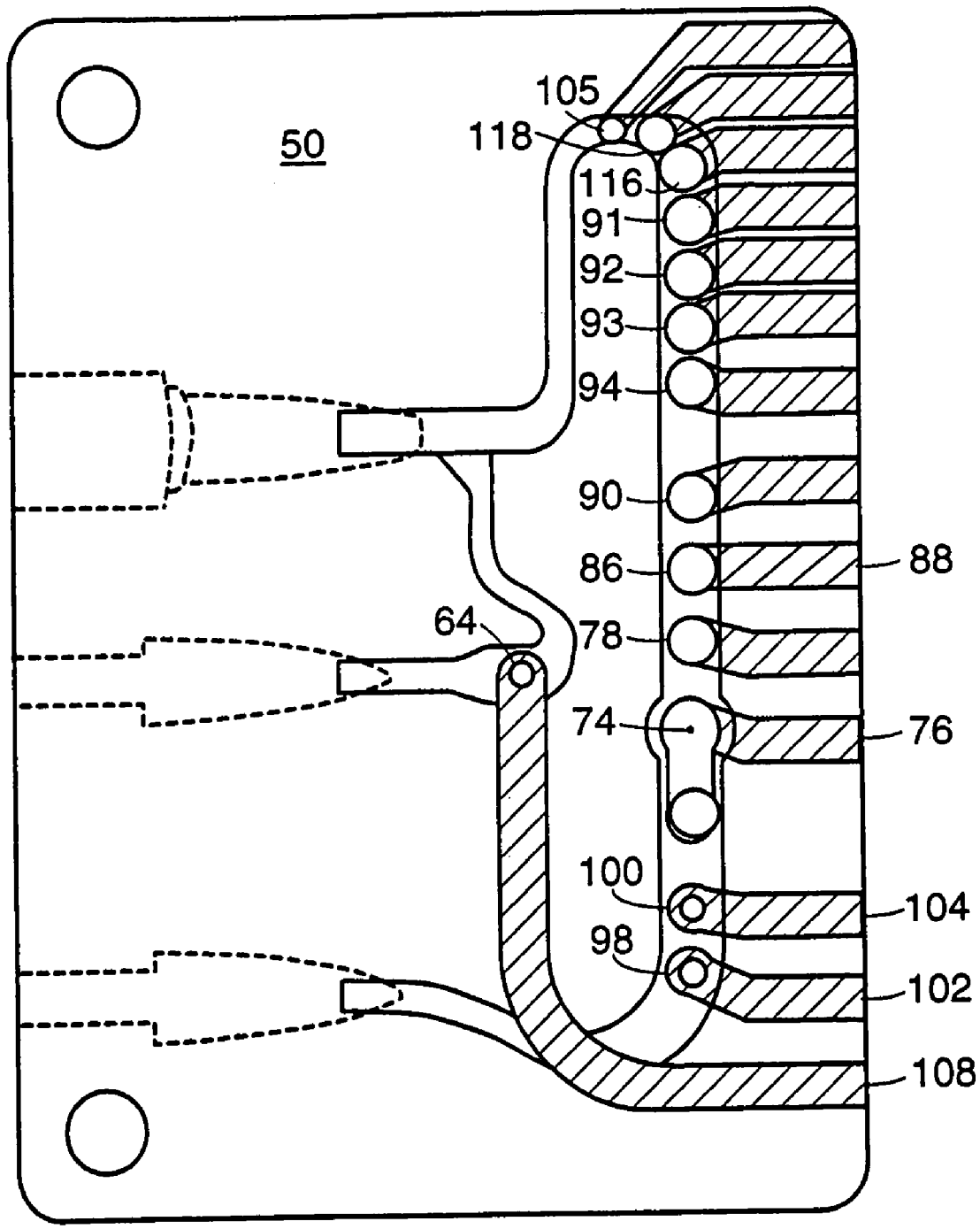
FIG. 5 illustrates a frontal view of the electrode card contained in one embodiment of the cartridge.

Referring to FIG. 2, a pair of gold wires 98 and 100 form electrodes for determining the hematocrit (Hct) of a sample based on its conductivity. The wires make contact with printed circuit edge connectors 102 and 104, respectively, also illustrated in FIG. 5.

The Oxygen Sensor

Figure 4:
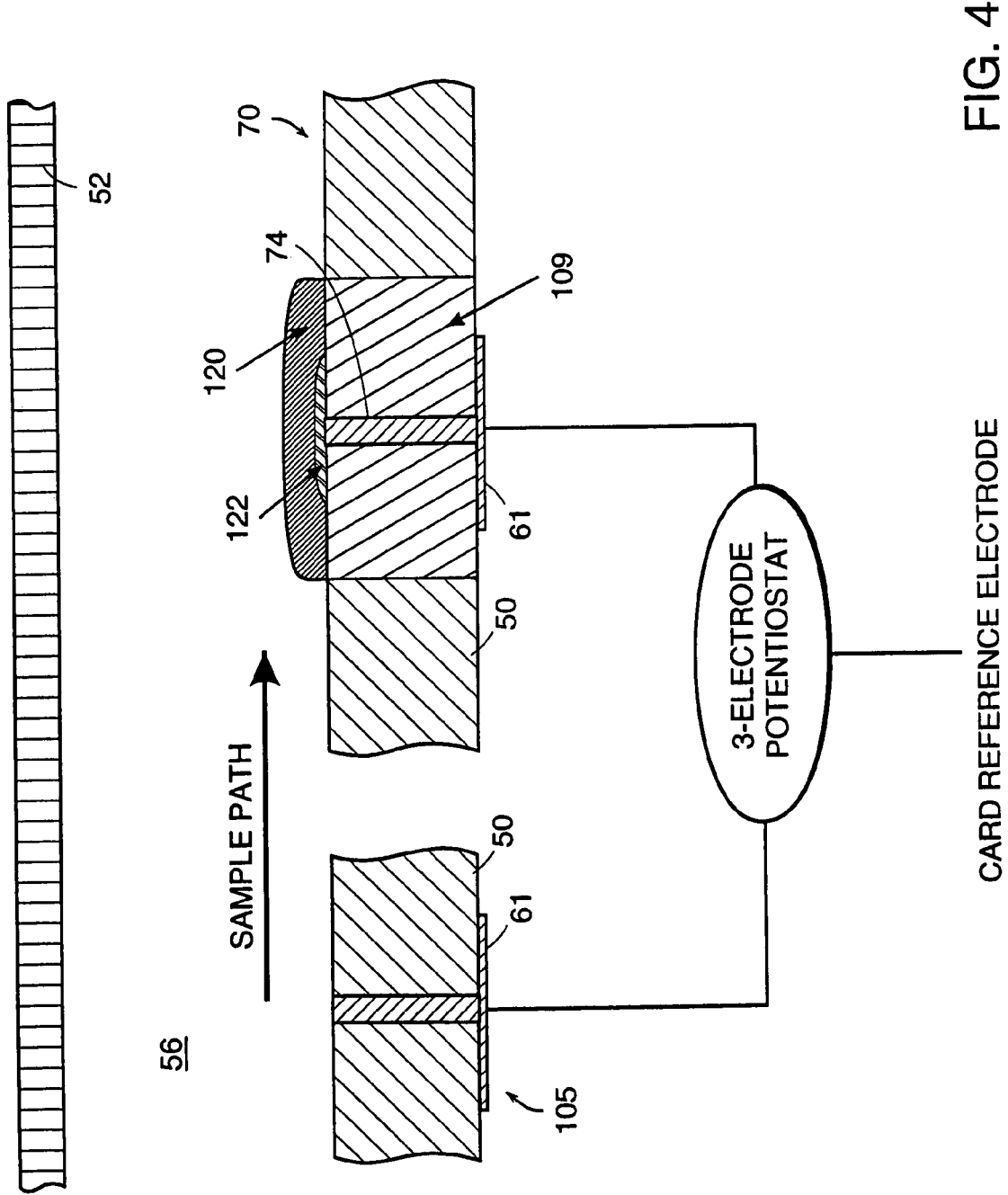
FIG. 4 illustrates an embodiment of a $pO_2$ sensor.

Referring to FIG. 2, the next sensor in the flow channel 56 is the oxygen sensor 70 with a three electrode configuration, also illustrated in FIG. 4.

The Potassium, Calcium and Sodium Ion Sensing Electrode

Next up the flow channel is a sodium sensing electrode 78, followed by a calcium sensing electrode 86 and a potassium sensing electrode 90 including an active membrane and a staked silver wire and an associated edge connector.

The pH Electrode

Figure 6:
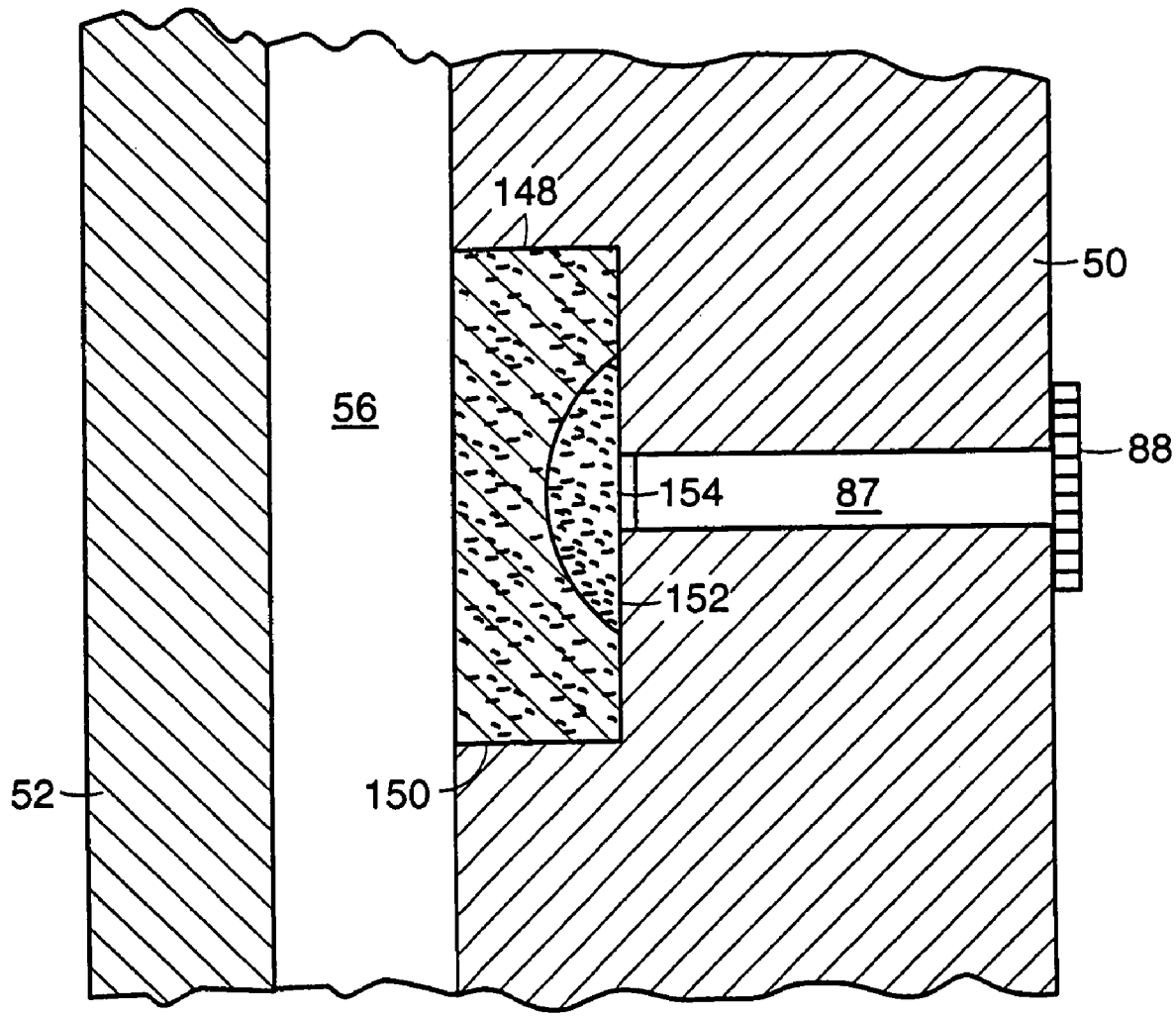
FIG. 6 illustrates cross-sectional views of an ion sensor.

Referring to FIG. 2, next along the flow channel 56 is a pH sensing electrode 94 also illustrated in FIG. 6 which includes a membrane 148 and a silver wire 87 staked or press-fitted through the thickness of the plastic 50 into the flow channel 56. Referring to FIG. 6, joined on the opposite side of the flow channel 56 is a pad printed conductor section 88 (also see FIG. 5) that forms an edge connector. The nature of this pH electrode will be subsequently described in detail.

The Carbon Dioxide Electrode

Referring to FIG. 2, the next electrode 93 along the flow channel 56 measures the dissolved carbon dioxide in the blood or calibrating solution and works in combination with the pH electrode 94.

The Lactate Electrode

Referring to FIG. 2, next along the flow channel 56, lactate electrode 92 functions by measuring by-products of an enzymatic reaction of lactate oxidase on lactate. The lactate oxidase present in the enzyme layer oxidizes the lactate producing hydrogen peroxide, which is detected by the electrode of the lactate sensor.

The Glucose Electrode

Referring to FIG. 2, a glucose electrode 91 is the next electrode, which like the lactate electrode 92 functions by the detection of hydrogen peroxide produced by an enzymatic reaction in the enzyme layer. The enzyme, glucose oxidase, specifically oxidizes glucose and produces hydrogen peroxide, a compound detected by the electrode of the glucose sensor.

The Creatine and Creatinine Electrodes:

Measurement of creatinine in a blood sample requires two electrodes. One electrode measures the total concentration of creatinine and creatine and the other electrode measures the concentration of only creatine. The concentration of creatinine is determined by subtraction of creatine from the combined creatine and creatinine concentrations. Referring to FIG. 2, the next two electrodes, creatinine 116 and creatine 118, which like the glucose electrode 91 and lactate electrode 92, function by detection of $H_2O_2$ produced by enzymatic reaction in their respective enzyme layers. In the creatinine electrode 116, the enzyme layer includes a mixture of three enzymes: creatininase, creatinase and sarcosine oxidase. This enzyme mixture specifically oxidizes creatinine and creatine and produces $H_2O_2$ in the following cascade reaction.

In the creatine electrode 118, the enzyme layer includes a mixture of two enzymes: creatinase and sarcosine oxidase. This enzyme mixture specifically oxidizes only creatine and produces $H_2O_2$ in the following cascade reaction:

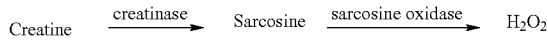

The Ground

The ground 105 illustrated in FIG. 2, is a silver wire inserted through the substrate 50. A ground serves as a common electric reference point for all electrodes. The ground may also serve as a counter electrode for the amperometric sensor system.

The Reference Electrode

As illustrated in FIG. 2, two silver wires 106 are staked through the thickness of the plastic substrate board 50 into the reference solution well 64 to act as the on-board reference electrode. Use of two silver wires 106 which are electrically connected assures continuous contact between the silver wire and the reference solution in the presence of air bubbles. Air bubbles may form in the reference channel as a result of degassing the reference solution at the elevated temperature of the sensor control. A printed circuit element 108, also illustrated in FIG. 5, extends along the back of the panel between the one end of this reference electrode and edge of the board to provide an edge connector.

The specific construction and operation of the electrodes will now be described in detail.

Specifics of Ion Selective Electrodes

The details of ion-selective electrodes are described, for example, in U.S. Pat. No. 4,214,968, incorporated by reference herein, and U.S. Pat. No. 4,734,184, incorporated by reference herein.

Ion-selective membranes of this type, which are also known as liquid membranes, constitute a polymeric matrix with a non-volatile plasticizer which forms the liquid phase in which an ion carrier or selector commonly referred to as an ionophore, which imparts selectivity to the membrane, is dispersed.

Ion-Selective Membrane Polymer

Polymers for use in the ion-selective membrane of the instant invention include any of the hydrophobic natural or synthetic polymers capable of forming thin films of sufficient permeability to produce, in combination with the ionophores and ionophore solvent(s), apparent ionic mobility thereacross. Specifically, polyvinyl chloride, vinylidene chloride, acrylonitrile, polyurethanes (particularly aromatic polyurethanes), copolymers of polyvinyl chloride and polyvinylidene chloride, polyvinyl butyral, polyvinyl formal, polyvinylacetate, silicone elastomers, and copolymers of polyvinyl alcohol, cellulose esters, polycarbonates, carboxylated polymers of polyvinyl chloride and mixtures and copolymers of such materials have been found useful. Films of such materials which include the ionophores and plasticizers may be prepared using conventional film coating or casting techniques and, as shown in the examples below, may be formed either by coating and film formation directly over the internal reference electrode or some suitable interlayer or by formation separately and lamination thereto.

Ionophore

The ionophore used in the ion-selective membrane is generally a substance capable of selectively associating or binding to itself preferentially a desired specific alkali metal, alkaline earth, ammonium or other ions. Suitable ionophores are more fully described below.

The selectivity of the electrode for a particular ion is due to the chemical nature of the ionophore and, thus, the use of different chemical components as the ionophore provides different membranes for use in ion-selective electrodes specific to different ions. Exemplary of such components are a large number of substances, some of them known to be antibiotics, which includes:

(1) valinomycin, a potassium-selective ionophore;
(2) cyclic polyethers of various constitution which make the membrane selective to lithium, rubidium, potassium, cesium or sodium; and
(3) other substances having ion selectivity similar to valinomycin such as other substances of the valinomycin group, tetralactones, macrolide actins (monactin, nonactin, dinactin, trinactin), the enniatin group (enniatin A, B), cyclohexadepsipeptides, gramicidine, nigericin, dianemycin, nystatin, monensin, esters of monensin (especially methyl monensin for sodium ion-selective membranes), antamanide, and alamethicin (cyclic polypeptides).

Numerous other useful materials are described in the foregoing publications and patents, as well as other literature on this subject.

The concentration of ionophore in the membrane will, of course, vary with the particular carrier used, the ion undergoing analysis, the plasticizer, etc. It has generally been found, however, that ionophore concentrations of below about 0.1 $g/m^2$ of membrane assuming the membrane thicknesses preferred herein result in marginal and generally undesirable responses. Ionophore concentrations of between about 0.3 and about 0.5 $g/m^2$ are preferred. The ionophore can be incorporated at levels much higher than this; however, because of the cost of many of these materials, use of such levels is not economically sound.

Plasticizer

The plasticizer provides ion mobility in the membrane and, the presence of a plasticizer is necessary to obtain good ion transfer.

The plasticizer must, of course, be compatible with the membrane polymer and be a solvent for the ionophore.

The other highly desirable characteristic is that the plasticizer be sufficiently insoluble in water that it does not migrate significantly into an aqueous sample contacted with the surface of the membrane as described hereinafter. Generally, an upper solubility limit in water would be about 4.0 g/l with a preferred limit lying below about 1 g/l. Within these limits, substantially any solvent for the ionophore which is also compatible with the polymer may be used. It is also desirable that the ion plasticizer be substantially non-volatile to provide extended shelf-life for the electrode. Among the useful solvents are phthalates, sebacates, aromatic and aliphatic ethers, phosphates, mixed aromatic aliphatic phosphates, adipates, and mixtures thereof. Specific useful plasticizers include trimellitates, bromophenyl phenyl ether, dimethylphthalate, dibutylphthalate, dioctylphenylphosphonate, bis(2-ethylhexyl)phthalate, octyldiphenyl phosphate, tritolyl phosphate, tris(3-phenoxyphenyl) phosphate, tris(2-ethylhexyl) phosphate, and dibutyl sebacate. Particularly preferred among this class are bromophenyl phenyl ether and trimellitates for potassium electrodes using valinomycin as the carrier.

A large number of other useful plasticizers permit assembly of electrodes of the type described herein and may be used in the successful practice of the instant invention.

The concentration of plasticizer in the membrane will also vary greatly with the components of a given membrane; however, weight ratios of plasticizer to polymer of between about 1:1 to about 5:2 provide useful membranes. The thickness of the membrane will affect electrode response as described in somewhat more detail below, and it is preferred to maintain the thickness of this layer below about 5 mils and preferably about 1 mil. As also described in greater detail below, the uniformity of thickness of the ion selective membrane plays an important role in the optimum utilization of electrodes of the type described herein. Thus, if maximum advantage in terms of storage capability is to be obtained, the ion-selective membrane should be of relatively uniform thickness as defined above.

Support

Referring to FIG. 1, the electrodes of the present invention include a support or card 50 which may be comprised of any material capable of bearing, either directly or by virtue of some intervening adhesion-improving layer, the other necessary portions of the electrode which are described in detail hereinafter. Thus, the support may comprise ceramic, wood, glass, metal, paper or cast, extruded or molded plastic or polymeric materials, etc. The composition of the support carrying the overlying electrode components must be inert; i.e., it does not interfere with the indicating potentials observed as, for example, by reacting with one of the overlying materials in an uncontrolled fashion. Moreover, the composition of the support must withstand elevated temperatures to which the sensors will be exposed, for the time length required to hydrate and/or calibrate the sensors. In the case of porous materials such as wood, paper or ceramics, it may be desirable to seal the pores before applying the overlying electrode components. The means of providing such a sealing are well known and no further discussion of the same is necessary here.

According to a highly preferred embodiment of the present invention, the support comprises a sheet or film of an insulating polymeric material. A variety of film-forming polymeric materials are well suited for this purpose; such as, for example, cellulose acetate, poly(ethylene terephthalate), polycarbonates, polystyrene, polyvinylchloride, etc. The polymeric support may be of any suitable thickness typically from about 20-200 mils. Similarly thin layers or surfaces of other materials mentioned above could be used. Methods for the formation of such layers are well known in the art.

Specifics of Enzyme Electrode

An enzyme sensor comprises a three-electrode system including a working, reference and counter electrode. The working electrode includes a composite membrane that is deposited on a surface in contact with a conductive wire, a platinum wire for example. The composite membrane comprises two or more layers, including a enzyme layer and an inner interference rejection membrane, for example.

The sensor fabrication may be based on solvent casting techniques well known in the art. The thickness of the layers can be controlled by dispensing precise volumes of solutes found in the layers. The polymeric membrane that comprises an inner interference rejection membrane, described in detail below, is formed onto the wire electrode by electropolymerization of electropolymerizable monomers, as described below.

Figure 3A:
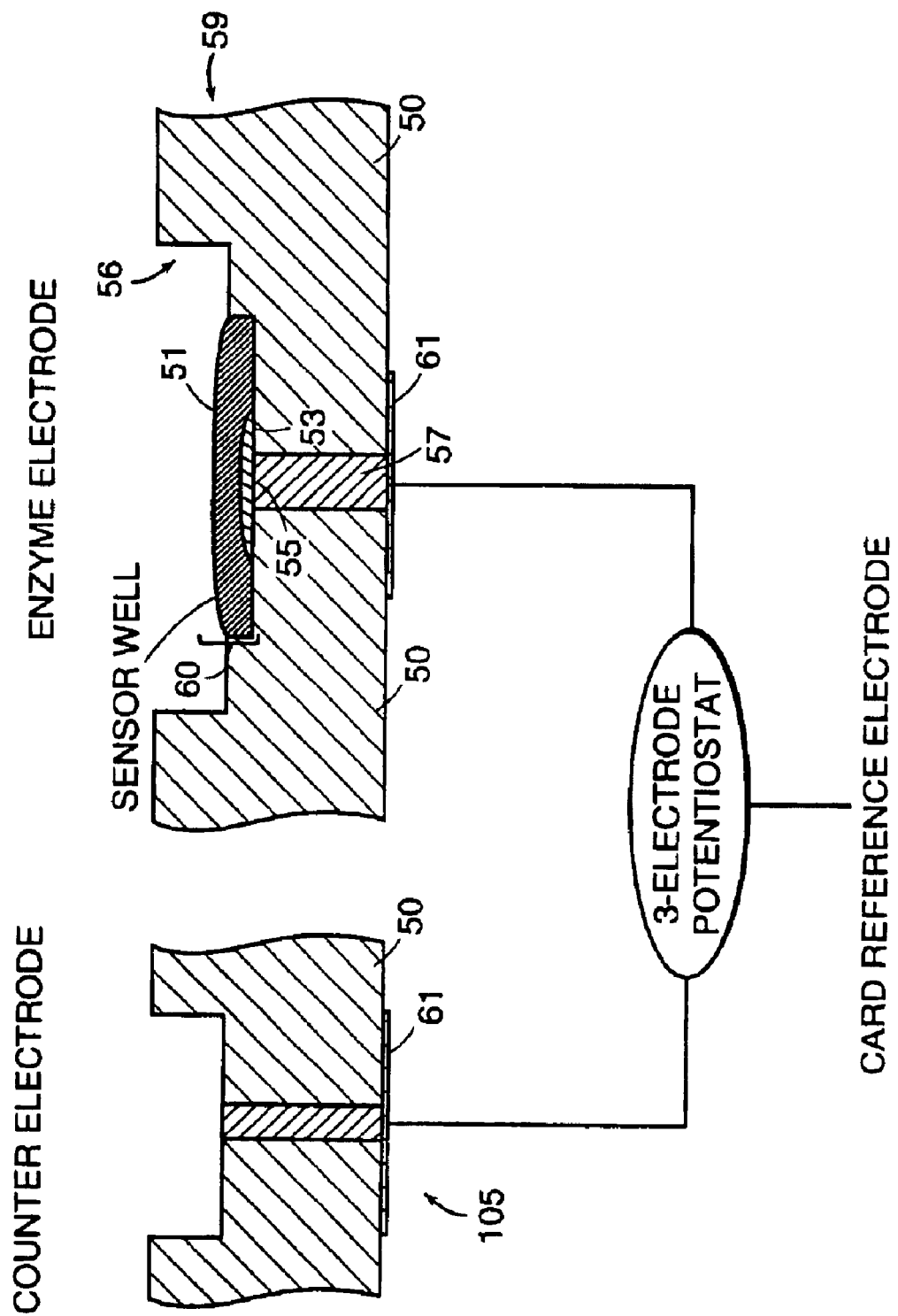
FIGS. 3A-B illustrate cross-sectional views of an enzyme sensor.
Figure 3B:
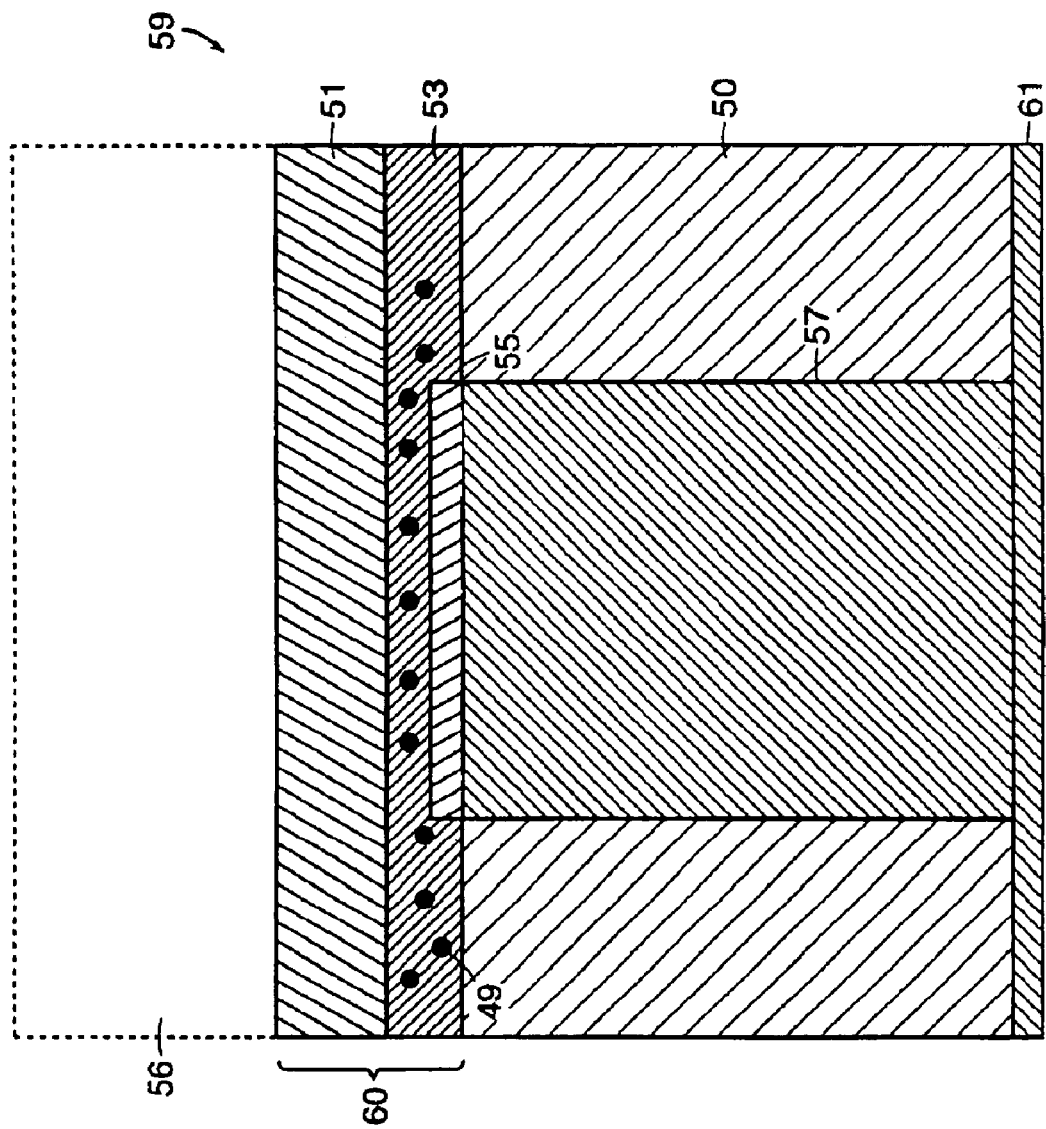

Referring to FIGS. 3A and 3B, an enzyme electrode 59, such as a glucose electrode, is located in the flow channel 56 of the sensor card 50. FIG. 3B is an enlarged section of FIG. 3A. The enzyme electrode 59 includes a three layer composite membrane 60 comprising, from the flow channel 56 to the wire 57, an outer membrane 51 adjacent to the flow channel 56, an enzyme layer 53, located between the outer membrane 51 and an inner interference rejection membrane 55 adjacent a wire 57. The enzyme-electrode 59 contacts the sample as the sample flows along the flow channel 56 and over the outer membrane 51 of the enzyme electrode 59. The electrical signal generated by the enzyme electrode 59 is carried by the wire 57 and transferred to the conductor 61 which is in electrical communication with the electrode assembly 10 shown in FIG. 2.

Referring still to FIGS. 3A and 3B, the outer membrane 51 of the enzyme electrode 59 generally functions to control the diffusion of the analyte into the enzyme layer 53 and to protect the other components of the electrode 59 from direct contact with constituents of the sample in channel 56. In one embodiment, the outer membrane 51 is a polymeric membrane comprising one or more polyurethane-based compounds. The hydrophobicity of the membrane is determined by the mixture of species of polymer compounds. As the hydrophobicity of the membrane increases, the ability of oxygen to diffuse through the membrane increases while the ability of analytes to diffuse through the membrane decreases. The preferred composition of the outer membrane 51 is the concentration in which an optimal balance of diffusion rates of oxygen, which is a required substrate of the enzymatic reactions, and analyte (lactate in a lactate sensor, or creatinine and creatine in a creatinine sensor, and glucose in a glucose sensor) exists under typical conditions. A highly hydrophobic outer membrane may be preferred because oxygen will diffuse quickly to the enzyme layer 53 and thus will not be a limiting factor to the enzymatic reaction. The outer membrane 51 may have a preferable thickness of 8 to 15 microns and could function with a thickness in the range of 5 to 30 microns.

The outer membrane 51 is composed of a blend of polyurethanes with different water uptake levels. A typical composition of the outer membrane 51 is 77% aliphatic, polyether-based polyurethane with 20% water uptake, 17% aliphatic, polyether-based polyurethane with 60% water uptake, and 6% aliphatic, polyether-based polyurethane with 3% water uptake. The outer membrane 51 with this composition can be produced by dispensing a volume from a solution of 3.0 mL cyclohexanone solvent, 17.0 mL tetrahydrofuran solvent, 1.08 g of 20% water uptake polyurethane, 0.24 g as 60% water uptake polyurethane and 0.08 g as 3% water uptake polyurethane onto the enzyme layer 53 of the composite membrane 60.

Referring to FIG. 3B, the outer membrane 51, which is layered directly onto and in contact with the enzyme layer 53, functions to preserve the enzyme layer 53 by preventing exposure of an enzyme 49 embedded in enzyme layer 53, and the stabilizing matrix in which the enzyme 49 is embedded, to degradatory proteins or compounds from the sample in channel 56. Likewise, outer membrane 51 prevents diffusion of the enzyme 49 out of the enzyme layer 53. The outer membrane 51 also functions to control the rate of diffusion of analyte (e.g. glucose, lactate, creatine and creatinine) and oxygen from the sample to the enzyme layer 53. Failing to control the diffusion of the analyte and oxygen to the enzyme layer 53 results in non-linear and inaccurate measurements of the analyte in the sample.

Referring still to FIG. 3B, the enzyme layer 53 of the glucose or lactate sensor, includes at least one enzyme 49 species required for the enzymatic reaction in which the specific analyte participates that is stabilized in the matrix of the enzyme layer 53. In one embodiment, the enzyme 49 includes at least one protein with enzymatic activity. In other embodiments, enzyme 49 includes a mixture of several enzymes, proteins and stabilizers, for example.

In a particular embodiment of the invention, the protein enzyme 49 glucose oxidase or lactate oxidase are embedded in the enzyme layer 53 and create an electrode 91 and 92 specifically sensitive to glucose and lactate, respectively, present in the sample. The glucose electrode 91 includes glutaraldehyde and glucose oxidase in the enzyme layer 53. In one embodiment, the glucose electrode 91 may include 0.10 g of glutaraldehyde per gram of glucose oxidase. In a particular embodiment, the lactate electrode 92 includes at least glutaraldehyde, bovine serum albumin, a enzyme stablizer such as, for example, polyethyleneimine and lactate oxidase in the enzyme layer 53. In one embodiment, the lactate electrode 92 includes 45% lactate oxidase by weight, 45% bovine serum albumin by weight, 5% polyethylenimine (an enzyme stabilizer) by weight and 5% glutaraldehyde by weight, for example. The weight fractions of lactate oxidase and bovine serum albumin can vary. The weight percent of polyethylenimine in the enzyme layer can vary from 1 to 20, and the weight percent of glutaraldehyde can vary from 1 to 10. Other enzymes stabilizers include but are not limited to polyionic compounds such as polypropyleneimine, poly(N-vinylimidazole), polyallylamine, polyvinylpiridine, polyvinylpyrollidone, polylysine, protamine and their derivatives.

In yet another embodiment of the invention, enzyme layer 53 includes a mixture of several enzymes, proteins, and stabilizers embedded in the matrix of enzyme layer 53 for specific detection of creatinine and creatine or creatine only. Enzyme mixtures are uised in the creatinine electrode 116 and creatine electrode 118. Creatine alone is detected with the creatine electrode 118. In a particular embodiment, creatinine electrode 116 includes a mixture of 5% creatininase by weight, 55% creatinase by weight, 30% sarcosine oxidase by weight, 5% poly(N-vinylimidazole) (an enzyme stabilizer) by weight and 5% glutaraldehyde by weight, for example. The weight fractions of creatininase, creatinase and sarcosine exidase in the creatinine electrode and the weight fractions of creatinase and sarcosine oxidase in the creatine electrode can vary. The weight percent of poly(N-vinylimidazole) in creatinine and creatine electrodes can vary, for example, from 1% to 20%, and the weight percent of glutaraldehyde in the creatinine and creatine electrodes can also vary, for example, from 1% to 10%. Polyionic stabilizers, other than poly(N-vinylimidazole), can also be used for stabilizing the enzyme mixture. Examples of polyionic compounds include but are not limited to polyethylenimine, polypropyleneimine, polyallylamine, polyvinylpiridine, polyvinylpyrollidone, polylysine, protamine, and their derivatives.

In one embodiment of the glucose, lactate, creatine, and creatinine electrodes, the enzyme layer 53 consists of a cross-linked matrix of enzymes, stabilizers such as polyethylenimine or poly(N-vinylimidazole), and other proteins such as bovine serum albumin. Cross-linking of the enzymes, stabilizers, and other protein molecules is accomplished with, for example, glutaraldehyde, a dialdehyde. Other cross-linking reagents, such as 1,4-diisocyanatobutane, a diisocyanato, 1,2,7,8-diepoxyoctane and 1,2,9,10-diepoxydecane, both diepoxides, can also be used. Cross-linking of the enzyme molecules and the use of the polyionic stabilizers and inert proteins in the enzyme matrix can, significantly extend the shelf-life and the use-life of the enzyme electrodes.

In yet another embodiment of the invention related to the creatinine 116 and creatine 118 electrodes, enzyme layer 53 includes a mixture of several enzymes, proteins, but lacks an enzyme stabilizer. In this embodiment, the creatinine electrode 116 includes a mixture of 30% creatininase, 30% creatinase, 30% sarcosine oxidase and 10% glutaraldehyde (percentages by weight). In this embodiment, the creatine electrode 118 includes a mixture of 45% creatinase, 45% sarcosine oxidase and 10% glutaraldehyde (percentages by weight). The enzyme layer 53 may have a thickness in the range of 1 to 10 microns, preferably 2-5 microns measured from the inner surface of the outer membrane 51 to the outer surface of the inner interference rejection membrane 55.

Referring to FIGS. 3A and 3B, the enzyme electrode 59 also includes an inner interference rejection membrane 55 which is a restorable polymeric membrane in close contact to the wire 57. The inner interference rejection membrane 55 may be formed by the polymerization of electropolymerizable monomers. Suitable electropolymerizable monomers include benzothiophene, phenylenediamines, and phenols, for example. The inner interference rejection membrane 55, which is typically less than a micron thick, insulates or protects the wire 57 from compounds in the sample, specifically oxidizable compounds, that interfere with the proper functioning of the enzyme electrode.

In one embodiment according to the invention, the polymeric membrane comprising the inner interference rejection membrane 55 is formed by the application of an electrical potential to the wire 57 in the presence of electropolymerizable monomers. The monomers in the presence of an electrical potential polymerize on the wire 57 to form an electrically insulating polymeric inner interference rejection membrane 55 on the wire 57 illustrated in FIGS. 3A and 3B. Hydrogen peroxide, which is generated from activity of the enzyme of the enzyme electrode on a specific analyte, passes through the pores of the inner interference rejection membrane 55 and contacts the wire 57 causing an electrical signal to be generated at the wire 57. The smaller size of the pores in the inner interference rejection membrane 55 restricts compounds found in the sample; larger than hydrogen peroxide, such as acetaminophen, ascorbic acid, uric acid, cysteine and other electroactive compounds that are larger than $H_2O_2$ from interfering with and reducing accuracy of the electrode 59 of the electrochemical sensor.

According to one embodiment of the invention, the inner interference rejection membrane 55 may be regenerated on a repeated basis to restore its function. Following repeated exposure to many samples, the inner interference rejection membrane 55 is degraded or fouled by compounds present in the sample. Degradation of the inner interference rejection membrane 55 is characterized by fissures in the polymeric structure of the inner interference rejection membrane 55. Such fissures prevent the ability of the inner interference rejection membrane 55 to protect the wire 57 from interfering compounds present in the analytical sample, e.g., ascorbic acid, acetaminophen, and uric acid, from contacting the wire 57 and altering the electrical signal detected by the wire 57.

In order to avoid problems induced by the degradation of the inner interference rejection membrane 55, an electropolymerizable monomer can be combined with a calibration solution, such as solution AO contained in the prepackaged container 23 of the electrochemical sensor system 8 illustrated in FIG. 1, for example, for use in the repolymerization and restoration of the inner interference rejection membrane 55. Polymerization of the monomer occurs when a monomer-containing AO solution is pumped from a prepackaged container and passed through the flow channel 56 on the sensor card 50 during the application of an electrical potential generated by electrochemical sensor apparatus 8 illustrated in FIG. 1 to the wire 57. During the polymerization process the monomer in the calibration solution in flow channel 56 diffuses through the outer membrane 51 and enzyme layer 53 until reaching the inner interference rejection membrane 55. Once at the inner interference rejection membrane 55 the monomers present in the solution enter the areas of the inner interference rejection membrane 55 that have lost structural integrity by degradation, splitting or cracking, and mediate the restoration of the inner interference rejection membrane 55 by polymerizing to fill in the damaged structure of the inner interference rejection membrane 55. The monomer is exposed to an electrical potential generated from an electrical source and transferred to the wire 57 in the areas of lost integrity of the inner interference rejection membrane 55. The electrical potential polymerizes the monomer onto the existing polymeric structure of the inner interference rejection membrane 55 at damaged areas of the inner interference rejection membrane 55 until the inner interference rejection membrane 55 is restored. Once the inner interference rejection membrane 55 is restored the insulating properties of the inner interference rejection membrane 55 is renewed and the monomer present at the inner interference rejection membrane 55 is sequestered from the electrical potential of the wire 57. This self-limiting restoration of the inner interference rejection membrane 55 is automatically repeated every 24 hours, for example. Regular, automatic, self-limiting restoration of the inner interference rejection membrane 55 ensures accuracy of the enzyme sensor 59. More or less frequent restoration cycles of the inner interference rejection membrane 55 can be employed to account for different situations.

The electrical potential for the polymerization process generated by the electrochemical sensor system 8 illustrated in FIG. 1 is applied to the wire 57 in the range of 0.1 to 0.8 V versus the on-board reference electrode 106, for about 30 seconds to one hour. An optimal polarization potential is 0.5 V versus the on-board reference electrode 106 for 3 minutes, repeated every 24 hours. The electrical potential is too low if it does not cause the polymerization reaction and the electrical potential is too high if it causes water hydrolysis and gas formation at the inner interference rejection membrane 55 thus causing damage to the enzyme electrode 59.

Specifics of the $PO_2$ Electrode

An oxygen sensor comprises a three electrode system including a working electrode, a reference electrode and a ground electrode. In one embodiment of the invention, the oxygen working electrode 70 comprises a platinum wire 74 that is fixed in the center of an insulative glass disk 109 and two protective membranes 120 and 122 best shown in FIG. 4. The disk preferably has a thickness of approximately 40 mils while the board 50 may have a thickness of approximately 85 mils. The diameter of the glass disk is preferably about 100 mils.

A number of the glass disks with the embedded platinum wires are prepared by inserting a close-fitting length of platinum wire into the lumen of a glass capillary tube and then melting the tube so that it fuses to the wire. After the tube with the embedded wire hardens, the disks of given axial thickness are sliced off, by a power saw, for example.

The glass disk is practically impervious to oxygen whereas the polyvinylchloride of the board 50 is relatively pervious. The glass disk thus protects the platinum electrode 74 from the gas so that only its distal end that faces the flow channel 56 is active.

The two membranes 120 and 122 on the glass disk protect the platinum wire 74 from direct contact with the constituents of the sample in channel 56. In one embodiment, the membrane 120 is a hydrogel based on methacrylic esters that is covalently bonded to the glass disk. The membrane 122 underneath the 120 covers only the area around the platinum wire and is made of polyvinyl alcohol. The composite membrane 60 including 120 and 122 provides a better protection and sensor performance than either of the membranes alone. The type of hydrogel that is employed is based on methacrylic esters, although hydrogels not based on esters of methacrylic acid may be used. To form a gel, the monomer, such as hydroxyethyl methacrylate or hydroxypropyl methacrylate, for example, is copolymerized with a cross-linker, such as, ethylene glycol dimethacrylate, diethylene glycol dimethacrylate or tetraethylene glycol dimethacrylate. The cross-linking reaction can be initiated by a photoinitiator such as dimethoxyphetlylacetophenone. A solvent such as ethylene glycol or water can be used to dilute reactions and control the viscosity of the solution.

It is of considerable advantage that the hydrogel membrane does not peel away from the surface of the oxygen electrode when the membrane hydrates. This is achieved by functionalization of the glass disk with methacrylic groups and cross-link the membrane to the surface. The surface of the glass disk is silinized with hexamethyldisilazane and functionalized with methacrylic groups by reacting with trimethoxysilyl propyl methacrylate.

After functionalization of the glass disk, a small drop of a solution of polyvinyl alcohol in water is dispensed at the center of the disk directly over the platinum wire and the water is allowed to evaporate for formation of the polyvinyl alcohol membrane. A solution of hydrogel component as described above is then dispensed on the disk in an amount corresponding to 50-micron thick film. The disk is exposed to a broad band UV light for 5 min to photopolymerized the hydrogel membrane.

The glass disk with the composite membrane on one side of it is embedded in a recessed form through the thickness of the plastic board 50 so that the non-hydrogel surface is flush with the surface of the board opposite the cover plate 52 and the hydrogel surface of the disk is flush with the bottom of the flow channel 56.

The oxygen sensor described here has several advantages when compared to the conventional electrode (Clark electrode), including smaller electrode size, simpler electrode fabrication, faster response time and longer use life. Separation of the reference and the counter electrodes form the working electrode allows for smaller size of the working electrode and simpler electrode fabrication. The oxygen response time is reduced because of the absence of internal solution and the resulting thinner membrane over the working electrode. The use of external reference electrode eliminates the silver dendrite formation on the working electrode, which is a common mode of failure in a Clark oxygen electrode with an internal Ag/AgCl reference electrode.

Concerning the amperometric function of the electrode in operation, a negative potential relative to the on-board reference electrode 106 is applied to the platinum wire 74 by the processor 40 which lessened potential serves to reduce any oxygen reaching its end and thereby produces an electrical current proportional to the oxygen diffusion through the layers 120 and 122 The hydrated layer 120 and 122 affords a reliable conductive flow path between the platinum electrode and the on-board reference electrode 106 to provide a polarization potential between the platinum and the solution in the hydrated layer. The resulting current flow between the platinum electrode 74 and the ground electrode is measured and is proportional to the oxygen concentration in the test fluid being monitored.

$pCO_2$, pH, Potassium Sodium and Calcium Sensing Electrodes

The electrodes, best illustrated generally in FIG. 2, connecting the silver wires 78, 86, 90, 93, and 94 which sense Na, Ca, potassium, $pCO_2$ and pH activities, respectively, are similar in construction. The difference is in the composition of the membrane layers. A typical ion-selective electrode is illustrated in FIG. 6. Each has a bead or an inner salt layer 152, which upon hydration forms the inner solution layer. This layer is in contact with the thin film of silver/silver chloride layer 154 obtained by anodization of the top of the silver wires. The outer layer 148 is essentially the polymeric ion-selective membrane layer. This layer is formed over the dried salt residue of the inner layer in a shallow well 150 as a dry residue remaining after the solvent removal from a matrix of a permeable hydrophobic membrane forming solution such as a solution containing polyvinylchloride, a plasticizer, an appropriate ion-sensing active ingredient and a borate salt. The outer membrane is applied as a solution, typically in Tetrahydrofuran (THF) in a small droplet. Once the solvent evaporates, the membrane is formed and is bonded to the plastic card. In the case of pH and $PCO_2$ electrodes, the ion-selective active ingredient may be tridodecylamine (TDDA) or a suitable pH sensing component. For the potassium electrode, a monocyclic antibiotic such as valinomycin may be used as the active ingredient. The calcium electrode employs a calcium ion-selective sensing component as its active ingredient such as (−)-(R,R)-N,N'-(Bis(11-ethoxycarbonyl)undecyl)-N,N'-4,5-tetramethyl-3,6-dioxaoctanediamide; Diethyl N,N'-[(4R,5R)-4,5-dimethyl-1,8-dioxo-3,6-dioxaoctamethylene]-bis(12-methylamino-dodecanoate) or other suitable calcium sensitive selective substance. The sodium electrode employs methyl monensin ester or any other suitable sodium sensitive active ingredient. The sodium, potassium and calcium electrodes use a buffer salt like MES (2-[N-morpholino]ethanesulphonic acid) along with the respective chloride salts for their inner solution.

pH and $pCO_2$ electrodes share the same outer layers, while their inner layers differ significantly. The internal layer for pH uses a strong buffer, for example, MES buffer, while that for $CO_2$ electrode use a bicarbonate buffer.

All ion-selective electrodes, except $CO_2$ electrode, operate through the measurement of the potential between the ion-selective electrode and the reference electrode 106 (FIG. 2), the change in potential is directly proportional to the change in the logarithm of the activity of the measured ion.

The $CO_2$ sensor is a combination of $CO_2$ and pH electrodes working together. In function the potential between the $CO_2$ and pH electrode is measured. The outer surface of both electrodes respond to pH in the same manner and cancel each other. The inner surface of the pH membrane has a high buffer with constant pH and does not cause any change in the measured potential. However, for $CO_2$, the membrane is freely permeable to $CO_2$, which dissolves in the bicarbonate buffer changing its pH. This causes a change in the potential response of the inner surface of the $CO_2$ membrane, which is the only change to the overall measured potential. Thus, the potential across the $CO_2$ and pH electrodes directly measures the variation in the $CO_2$ concentrations of the sample.

The process of hydrating the inner salt layer in these ion-selective electrodes is achieved by soaking the outer surface of the outer membranes in an aqueous salt solution, usually a calibrating reagent solution. The hydration, however, is a very slow process, as the water has to permeate through the hydrophobic outer membrane in the vapor form. Thermal cycling through high temperatures facilitates the process. During the process of thermal cycling, the composition and integrity of the membrane layers stay intact.

Hydration and calibration of the ion sensing electrodes are accomplished by steps similar to those described for the $pO_2$ electrode. Hydration from a dry state can be accelerated by soaking the sensors in an electrolyte solution, such as the calibrating solutions described above, and thermally cycling the sensors through an elevated temperature higher than that of normal use. For example, the sensors are soaked in calibrating solution B at a temperature between 55° C. to 75° C. for 15 minutes, and then cooled to 37° C. The calibration cycles start as soon as the temperature reaches 37° C. In a preferred embodiment, the sensors are soaked in a calibrating solution at a temperature of 60° C. for 12 minutes, and then cooled to 37° C. The calibration cycles start as soon as the temperature returns to 37° C.

Hematocrit Measurement

The hematocrit (Hct) measurement is made through a measurement of resistivity between gold wires 98 and 100. The sensor operates by measuring the resistivity of the solution or blood sample placed between the electrodes. Hematocrit is calculated as a function of resistivity using the Maxwell equation.

Removal of Interfering Agents

Exposure of the enzyme electrode 59 to the sample in the flow channel 56 causes the composite membrane 60 to retain residual concentrations of substrate from the sample and products of the enzymatic reaction from the operation of the enzyme electrode 59. These substances are examples of the interfering agents that will cause the enzyme electrode 59 to lose accuracy and precision in measurement of the specifically intended analyte. In order to restore accuracy and precision to the enzyme electrode 59, interfering agents are removed from the composite membrane 60 of the enzyme electrode 59 by applying an additional amplitude of polarization to the wire 57 of the enzyme electrode 59.

A polarization pulse may be applied by an electrical source to the wire 57 after each exposure of the electrode 59 to a sample in order to prepare the electrode 59 for the next measurement. For example, hydrogen peroxide, a product of the reaction of the enzyme and the analyte from the operation of the electrode 59, is an example of an interfering agent. To remove interfering agents such as hydrogen peroxide, an additional amplitude of polarization is applied to the wire 57 which causes oxidation of the interfering agent. Oxidation of the interfering agent renders the interfering agent incapable of affecting the electrical activity at the wire 57 by effectively removing the agents from the electrode 59. The analytes, such as glucose and lactate, also constitute interfering agents when residual concentrations of glucose and lactate remain in the enzyme electrode 59 between sample readings. A polarization pulse applied to the wire 57 oxidizes the residual analyte and thus eliminates contribution of residual analyte between samples to erroneous analyte measurements.

In one embodiment according to the invention, after measurement of an analyte in a sample is complete, the enzyme electrode 59 is restored by pumping the sample out of the flow channel 56, and a volume of wash solution from reservoir 17 is pumped through the flow channel 56. During this time, an additional polarization is superimposed on the stable polarization continuously applied to the electrodes 59 after a sample measurement. The polarization is then returned to its baseline level and a calibration solution is introduced into the flow channel 56 followed by a one-point calibration to ready the electrode 59 for the next measurement.

The sufficient amplitude and duration of the polarization pulse required for the oxidation of interfering agent is determined by the geometry of the flow channel 56. Greater pulse amplitudes and longer pulse durations are required for an electrode 59 with a narrow flow channel 56 and a slow flow rate of wash solution. In a preferred embodiment illustrated in FIG. 3A, a polarization amplitude of 0.4 V versus the on-board reference electrode for a duration of 50 seconds is sufficient to eliminate interfering compounds from the composite membrane 60, and thus improve accuracy and precision of the electrode 59 measurements. A polarization amplitude in the range from 0.1 to 0.8 V versus the on-board reference electrode for a duration of 10 to 200 seconds may also be sufficient.

Restoration of the Inner (Interference Rejection) Membrane of the Composite Membrane A further step to restore the function of the inner interference rejection membrane 55 of the composite membrane 60 of the enzyme sensor 59 illustrated, for example, in FIG. 3B. This step includes restoration of the integrity and proper functioning of the inner interference rejection membrane 55 of the enzyme electrodes. Within the composite membrane 60, illustrated in FIG. 3B restoration of the inner interference rejection membrane 55 occurs by the in situ polymerization of electropolymerizable monomers onto the inner interference rejection membrane 55 of the composite membrane 60.

In one embodiment, the electropolymerizable monomers are in solution in the AO calibration solution in container 23 illustrated in FIG. 1 The AO calibration solution is passed through the flow channel 56 of the sensor card 50 illustrated in FIG. 3A. The AO solution with the electropolymerizable monomers contact the enzyme electrode 59 at the outer polymeric membrane 51 of the composite membrane 60. The electropolymerizable monomers diffuse first through the outer membrane 51, and then through the enzyme layer 53 of the composite membrane 60, until the monomers reach the inner interference rejection membrane 55 of the composite membrane 60. An electrical potential greater than baseline, 0.5 V versus the on-board reference electrode for is applied to the wire 57 for 3 minutes, for example, causing the electropolymerizable monomers to polymerize onto the existing polymeric structure of inner interference rejection membrane 55 of the composite membrane 60. Following the polymerization of the inner interference rejection membrane 55, the insulating properties of the inner interference rejection membrane 55 are restored. Because the remaining electropolymerizable monomers in the calibration solution are no longer exposed to the electrical potential, polymerization of the monomers can no longer occur.

The amplitude of the electrical potential and the period of time of the elevated potential sufficient for restoration of the inner interference rejection membrane 55 of the composite membrane 60 is determined by the specific configuration of the electrode 59. The composition and the particular geometry of electrode affects the amplitude of the electrical potential and the period of time required for complete restoration of the inner interference rejection membrane 55. A composite membrane 60 of a composition or geometry that slows the diffusion of monomers from the flow channel 56 to the inner interference rejection membrane 55 will require a greater polymerization amplitude for a greater duration of time. A polarization of about 0.1 to 0.8 V versus an on-board reference electrode applied for about 30 seconds to 1 hour is suitable for at least partial restoration of the inner interference rejection membrane 55. Once the restoration of the inner interference rejection membrane 55 is complete, the AO solution in flow channel 56 is replaced with rinse solution 17 and the electrical potential is returned to baseline.

Reference Solution Operation

Referring to FIG. 2, as has been noted, the reference solution fills the well 64 where it contacts a silver wire 106 and is pumped through the capillary channel 66 to join the outlet of the main flow line. The reference solution is essentially a hypertonic solution of potassium nitrate, with respect to the blood or the calibrating solutions and accordingly the domain of the reference electrode 106 constitutes a stable potential liquid junction formed between the reference electrode and the blood or calibrating solution, thereby establishing an environment that is independent of the ionic activity of the blood or calibrating solution.

Since the reference solution joins the main flow channel downstream from the electrodes, it does not affect those measurements in any way. The reference solution is of high density and under pumping force must flow upward against gravity to the outlet. Thus, when the pump stops, as for electrode equilibration, the reference solution remains stationary in the reference well 64 and the capillary section 66 and tends not to diffuse into the calibrating solution or blood in the main flow channel. Thus, the capillary tube 66 due to the density gradient, acts as a one way valve allowing pumped reference solution to pass upwardly through the capillary but preventing unwanted reverse passage or mixing of the blood or calibrating solution into the reference well.

Heater Block Assembly

Referring to FIGS. 7A-7G, the heater block assembly 39 includes a thermoelectric device 230, a thermistor 41, an aluminum block featuring two aluminum shells 220a, 220b, electrode interface 156, metal plate 234, heat sink 236, electrical leads 229, 229', 231, 231', and cable 226. The aluminum block houses a sensor card 10 when the cartridge with the sensor card is inserted into the fluid analysis instrument 8.

Figure 7A:
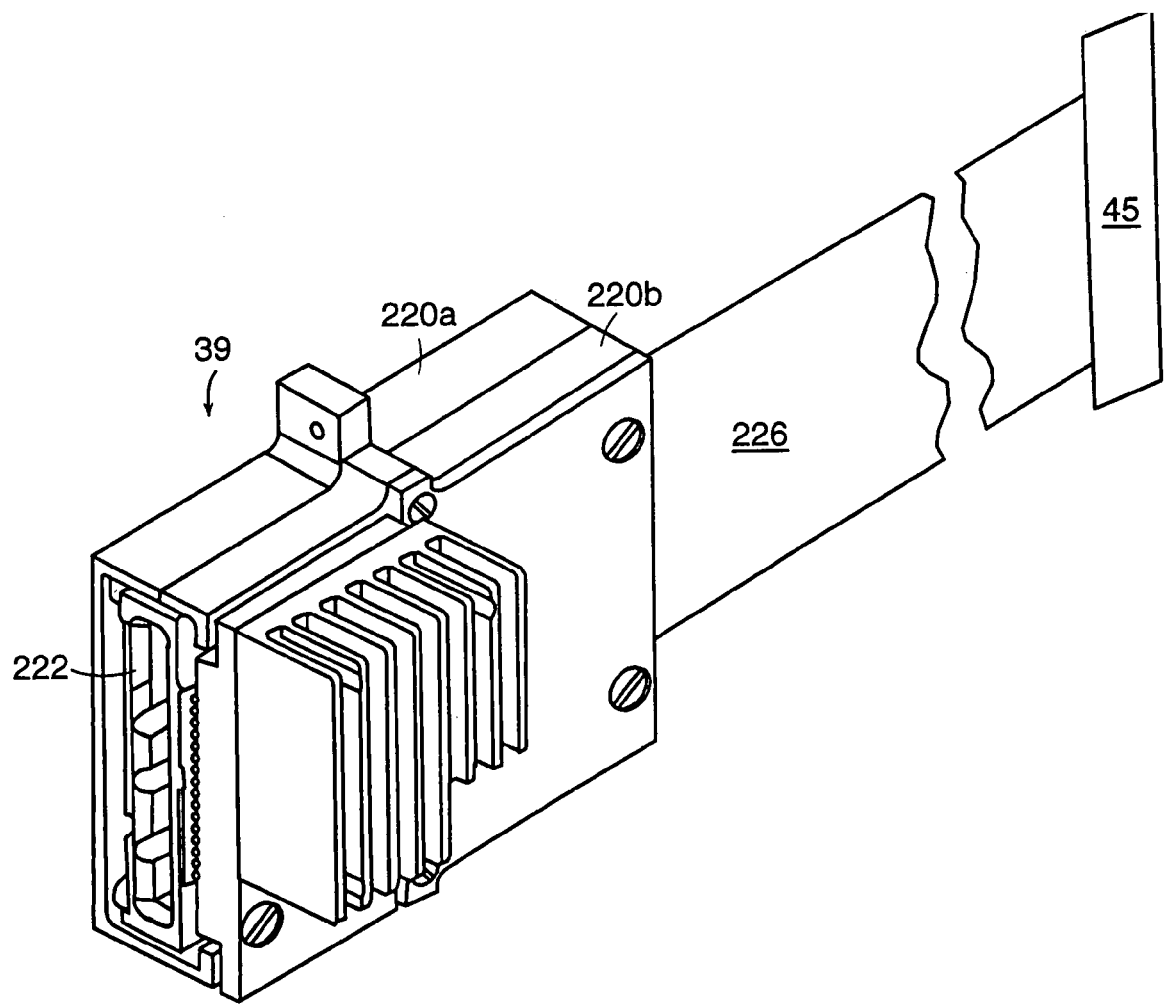
FIGS. 7A-G illustrate the components of a thermal block assembly.
Figure 7B:
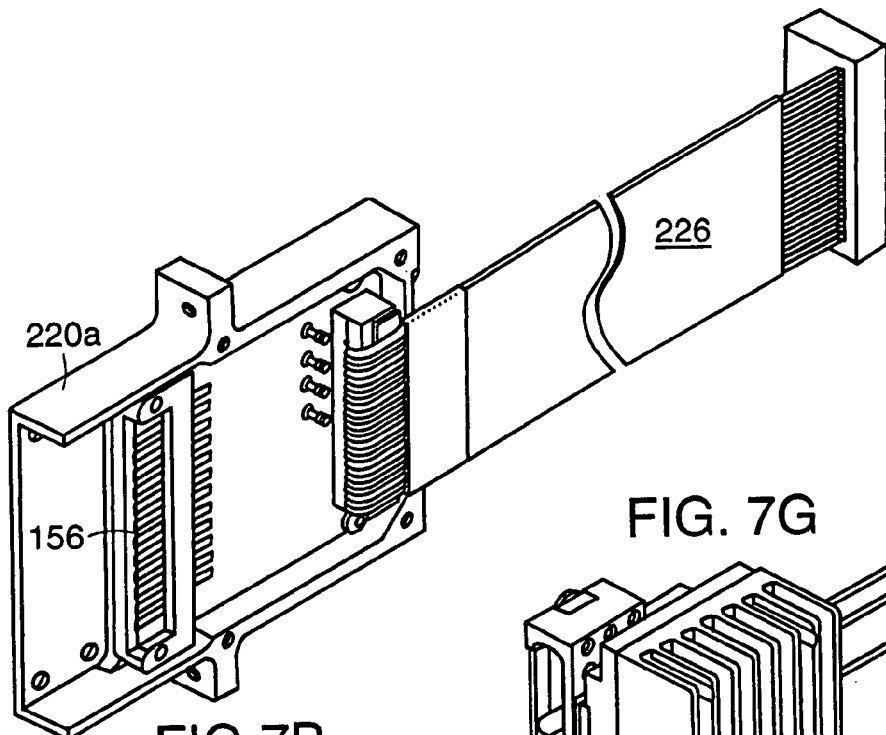

Referring to FIG. 7A, the aluminum heater block assembly 39 includes two aluminum shells 220a, 220b which together form a socket 222 into which a sensor card 10 (not shown) can be inserted. As illustrated in FIG. 7B, electrical connection 156 located in socket 222, interfaces with the corresponding edge connectors in the sensor card illustrated in, for example, FIG. 5, to transmit signals from the sensors. A cable 226 connects the electrical connectors from the sensor card to a microprocessor 40 through an analog board 45 (See FIG. 1). A printed circuit board (analog board located before the processor) controls the sensors and measures sensor output. Printed circuit boards within this heater block assembly contain post amplifiers that amplify signals from the sensor in the sensor card. The output of the sensors are analog signals. The analog signals are converted to digital signals via an analog to digital converter, and the digital signals are transmitted to the microprocessor for storage, analysis, and display.

Figure 7G:
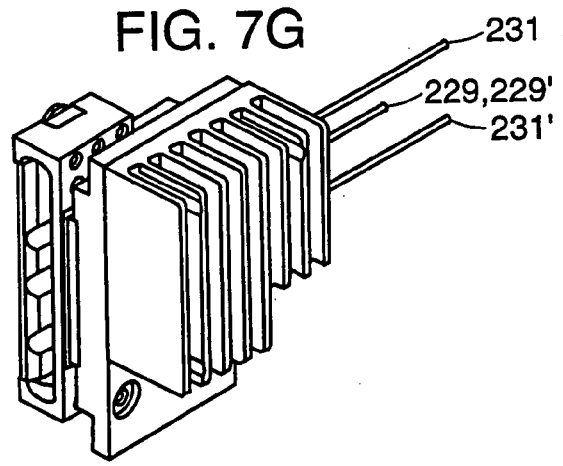
Figures 7C, 7D, 7E, 7F:
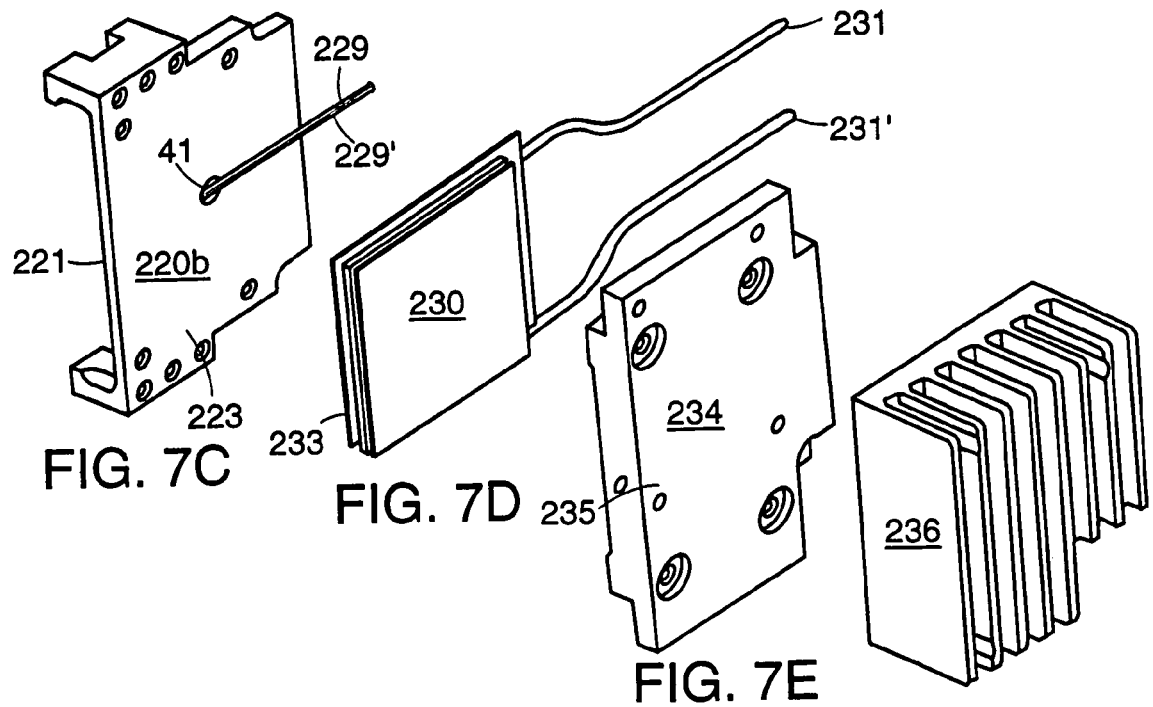

Referring to FIG. 7C, the interior surface 221 of aluminum shell 220b comes into contact with the metal plate 52 of a sensor cartridge 10 (see FIG. 2). On the external surface 223 of aluminum shell 220b, a thermistor 41 is located as illustrated in FIG. 7C. Extending from thermistor 41 are electrical connections 229, 229' that connect the thermistor 41 to a microprocessor 40.

On top of the external surface 223 of aluminum shell 220b and over the thermistor 41, a thermoelectric device 230 illustrated in FIG. 7D, is positioned. Thermoelectric devices in the heater block assembly may use, for example, the Peltier-effect, to heat and cool the aluminum block. Electrical leads 231, 231' supply programmed electrical current controlled by a microprocessor 40 to the thermoelectric device 230. The direction and duration of current is controlled by the microprocessor 40 and determines whether the thermoelectric device 230 overlying the aluminum shell 220b is in a warming or cooling mode. The temperature of the aluminum shell 220b is measured by thermistor 41 which transmits signals to microprocessor 40. Microprocessor 40 is programmed to transmit electrical signals to the thermoelectric device, depending on signals from the thermistor, to either heat or cool the aluminum shell 220b which in turn heats, cools or maintains the temperature of a sensor card inserted into socket 222. When current flows in the thermoelectric device 230 in the forward direction, the metal plate 220b is heated and this heat is transmitted to the sensor card in the socket 222. When current flows in the reverse direction, the metal plate 220b is cooled and the cooling effect is transmitted to the sensor card in the socket 222.

Referring to FIGS. 7D and 7E, the external surface 233 of the thermoelectric device 230 is in contact with a metal plate 234. The external surface 235 of metal plate 234 is in contact with a heat sink 236, illustrated in FIG. 7F.

The assembled cartridge socket 222, aluminum shell 220b, thermistor 41, thermoelectric device 230, metal plate 234, heat sink 236 and electrical leads 229, 229' from the thermistor 41, and electrical leads 231, 231' from the thermoelectric device 230 to the microprocessor 40 is illustrated in FIG. 7G.

In a preferred embodiment of the heater block assembly 39, the temperature for a sensor cartridge can be increased from about 37° C. to about 60° C. to 65° C. in one minute, maintained at 60° C. for 12 minutes with only 1.0° C. temperature fluctuation, and cooled to 37° C. from 60° C. in about two minutes.

Initial Operation of the Assembly

Referring to FIG. 1, when the cartridge with the sensor assembly 10 and the filled bags 14, 16 and 28 are first used, the valve 18 is controlled to direct one of the calibration solutions for example, calibration solution B, into the sensor assembly so it entirely fills the flow channel. The pump is then stopped for a period of 10-30 minutes, preferably 12-15 minutes during which the dry chemical sensor electrodes are hydrated by thermal cycling, for example, from 37° C. to 60° C. and back to 37° C.

In one embodiment of the invention, the dry chemical electrode sensor assembly 10 is inserted into the electrochemical sensor system 8 and the valve 18 is controlled by microprocessor 40 to direct the calibration solutions B into the sensor assembly 10. Thermal block assembly 39 is set at a temperature whereby the temperature of thermal plate 52 is sufficient to heat the calibrating solution in contact with the dry chemical sensor to a temperature in a range of 55° C. to 75° C., preferably 60° C., for 10-30 minutes, preferably 12 minutes. After the specified time period, the microprocessor 40 reverses current flow through the thermoelectric device to cool thermal plate 52. The sensor card 50 and calibrating solution in contact with thermal plate 52 are cooled to 37° C. The temperature, controlled by the microprocessor 40, is maintained at 37° C. for the life of the cartridge 37. After hydration of the sensors, the conditioning cycle of the enzyme electrodes 59 starts by pumping the AO solution 23 to the sensor card 50 and soaking the electrodes 59 for 1 to 6 minutes, preferably, for 3 minutes while the polarization potential of the enzyme electrodes 59 is elevated from 0.25 to 0.5 V versus the on-board reference electrode. During the AO exposure, the inner interference rejection membrane 55 of the enzyme electrodes 59, illustrated in FIG. 3B, is restored. Moreover, in this cycle the low oxygen level is also calibrated. Upon completion of the AO cycle, the rinse cycle starts by pumping rinse solution from prepackaged container 17 the flow channel 56 by the peristalic pump 26. During the rinse cycle the polarization potential of the enzyme electrodes 59 is changed from 0.5 to 0.4 V in order to accelerate the removal of the AO residues from the inner interference rejection membrane 55. Following the completion of the rinse cycle, the polarization potential of the enzyme electrodes 59 are lowered back to normal level of about 0.25 V versus the on-board reference electrode. A calibration cycle with solutions A 14 and B 16 then begins. The cartridge 37 becomes ready for sample measurement within 30 minutes of cartridge 37 insertion into the electrochemical sensor system 8.

What is claimed is:

1. A method for removing interfering agents from a composite membrane comprising:
   providing an electrochemical sensor comprising an electrode, said electrode including a composite membrane disposed thereon, said composite membrane comprising two or more layers;
   providing an electrical source in electrical contact with said electrode;
   exposing the electrode to a first sample;
   measuring a signal generated by the first sample by use of the electrical source;
   replacing the first sample with a rinse solution after said measuring; and
   applying an electrical potential with the electrical source to said electrode while exposing the electrode to said rinse solution, wherein the electrical potential is sufficient to cause at least a portion of the interfering agents in said composite membrane to be oxidized and removed.

2. The method of claim 1, wherein said range of electrical potential is applied for about 10 to 200 seconds.

3. The method of claim 1, wherein said electrical potential comprises about 0.4 V versus an on-board Ag/AgNO$_3$ reference electrode and is applied for about 50 seconds.

4. The method of claim 1, wherein the composite membrane comprises an enzyme layer and an inner polymeric layer.

5. The method of claim 4, wherein the enzyme layer comprises one or more H$_2$O$_2$ generating enzymes.

6. The method of claim 4, wherein the enzyme layer comprises one or more enzymes selected from glucose oxidase, lactate oxidase, creatininase, creatinase, and sarcosine oxidase.

7. The method of claim 4, wherein the enzyme layer comprises glucose oxidase.

8. The method of claim 4, wherein the enzyme layer comprises lactate oxidase.

9. The method of claim 4, wherein the enzyme layer comprises creatinase and sarcosine oxidase.

10. The method of claim 9, wherein the enzyme layer comprises creatininase.

11. The method of claim 1, wherein said electrical potential comprises a range of about 0.1 to 0.8 V versus an on-board Ag/AgNO$_3$ reference electrode.

12. The method of claim 1, wherein the rinse solution is a calibration solution.

13. The method of claim 1, wherein the composite membrane is an electrically insulating membrane.

14. A method for removing interfering agents from a composite membrane comprising:

providing an electrochemical sensor comprising an electrode, said electrode including a composite membrane disposed thereon, said composite membrane comprising at least one polymeric layer;

providing an electrical source in electrical contact with said electrode;

applying an electrical potential with the electrical source to said electrode sufficient to cause at least a portion of the interfering agents in said composite membrane to be oxidized and removed; and measuring a signal generated by the electrode by use of the electrical source, wherein the electrical source is in electrical communication with the electrode during the measuring of the signal and the removal of interfering agents from the composite membrane, and wherein said electrical potential comprises a range of about 0.1 to 0.8 V versus an onboard Ag/AgNO$_3$ reference electrode.

* * * * *